United States Patent [19]

Boaz

[11] Patent Number: 5,312,950

[45] Date of Patent: May 17, 1994

[54] METHOD FOR PURIFICATION OF ALCOHOLS

[75] Inventor: Neil W. Boaz, Waterloo, N.Y.

[73] Assignee: Eastman Kodak Company, Rochester, N.Y.

[21] Appl. No.: 114,808

[22] Filed: Aug. 31, 1993

[51] Int. Cl.$^5$ .................... C07C 303/02; C07C 69/76; C07C 29/74

[52] U.S. Cl. ........................................ 558/51; 560/60; 560/183; 568/300; 568/675; 568/700; 568/810

[58] Field of Search .................. 558/75; 568/300, 675, 568/700, 810; 560/60, 183

[56] References Cited

PUBLICATIONS

Abstract, *Enzymic Manufacture of Optically Active Primary Alcohols*, Achinami et al, Jpn. Kokai Tokkyo Koho, 8 pp., Jp 02227097 A2 Sep. 10, 1990 Heisei.

Chem. Pharm. Bull. 36(6) 1653–1655(1989) *Facile Process for Enzymic Resolution of Racemic Alcohols*, Terrao, et al.

Tetrahedron vol. 47, No. 32, pp. 6223–6230, 1991 *Lipase-Catalyzed Kinetic Resolution of Methyl 4-Hydroxy-5-Tetradecynoate and its Application to a Facile Synthesis of Japanese Beetle Pheromone*, Fukusaki et al. Tetrahedron Letters, vol. 29, No. 14, pp. 1717–1720, 1988, *Asymmetric Ring Opening of Cyclic Acid Anhydrides with Lipase in Organic Solvents*, Yammoto et al.

*Primary Examiner*—Mary C. Lee
*Assistant Examiner*—Joseph K. McKane
*Attorney, Agent, or Firm*—Judith A. Roesler; J. Jeffrey Hawley

[57] ABSTRACT

A method for the purification of alcohols from organic soluble impurities has been discovered comprising treating the crude alcohol with a cyclic anhydride followed by an aqueous base and extracting the corresponding half-ester into aqueous solution leaving the impurities in organic solution. This method is particularly useful for the separation of chiral, nonracemic alcohols from the corresponding antipodal ester (the mixture resulting from an enzymatic kinetic resolution) because the separation is non-chromatographic and the enantiomeric integrity of the products is maintained.

17 Claims, No Drawings

METHOD FOR PURIFICATION OF ALCOHOLS

FIELD OF THE INVENTION

The present invention relates to a method for the purification of alcohols. Although general in scope, this method is particularly useful for the separation of chiral, nonracemic alcohols from the corresponding antipodal ester (the mixture resulting from an enzymatic kinetic resolution) because the separation is non-chromatographic and the enantiomeric integrity of the products is maintained.

BACKGROUND OF THE INVENTION

Purification as used herein encompasses the separation of an alcohol from other inert contaminants. Although a number of purification techniques for alcohols are known, the separation of a desired alcohol from closely related species is still difficult, especially on a large scale. As known, alcohols are valuable commodity chemicals with a wide range of uses, such as, for example, synthetic intermediates. Simple and versatile methods for purification that may be easily commercialized are badly needed.

One area of particular need is in the separation of chiral, nonracemic alcohols from their corresponding antipodal esters, the mixture of which may result from an enzymatic kinetic resolution. These enzymatic resolution methods typically include enzymatic hydrolysis, transesterification, or esterification. The separation of the antipodal ester from the racemic alcohol is particularly challenging because they are closely related species and the optical purity of product and/or substrate must be substantially maintained. The resulting separated compounds are of growing interest to the pharmaceutical, agricultural, and fragrance industries as optically active synthetic intermediates and building blocks.

There are several known methods for separating enzymatic resolution product mixtures. One known method is used for systems in which the chiral center resides in the carboxylate portion of the molecule (rather than the alcohol portion of the molecule), as shown in Figure I-1, below. In these systems, the enzymatic kinetic resolution (hydrolysis) results in a mixture of the unreacted ester and the corresponding antipodal carboxylic acid. Separation of the product carboxylic acid from the unreacted ester is usually accomplished simply by aqueous base extraction. For enzymatic resolution products where the chiral center resides in the alcohol portion of the molecule, (as shown in Figure I-2, below) separation is often accomplished by liquid chromatography. This technique, however, is generally only useful for small scale operations. Both reaction schemes are shown below in Figure I where R represents general organic substituents.

FIGURE I

(1)

OR

(2)

In another known technique, separation is accomplished by the formation of a water-soluble ester during an enzymatic esterification reaction followed by extractive separation of the water-soluble ester from the residual alcohol (Terao, et al. *Chem Pharm Bull.* 1989, 37, 1653; Achinami, et al., Jpn Kokai Tokyo Koho, JP 89-45339, CA114(15):141642v), as shown below in FIGURE II, where R*—OH represents 2,2-dimethyl-1,3-dioxolane-4-methanol, 2,2-diethyl,3-dioxolane-4-methanol, 2,2-dibenzyl-1,3-dioxolane-4-methanol, 2,2-diphenyl-1,3-dioxolane-4-methanol, 5-hydroxymethyl-3-isopropyloxazolidin-2-one, 1-phenylethanol, 2-octanol, or, generically, $R^xR^yR^zCCH_2OH$ where $R^x=OR'$ or $NR'_2$ and $R^y$ and $R^z$ are H, halide, etc. ($R'=H$, hydrocarbyl, acyl).

FIG. II

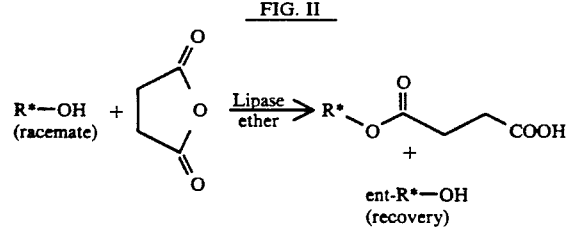

Because the method described in Figure II utilizes an anhydride as the acyl donor for the enzyme, this method is generally limited to enzymatic esterifications and is not typically useful for enzymatic hydrolysis or transesterification reactions. An additional limitation of this method is that highly reactive alcohols could exhibit significant non-enzymatic (achiral) esterification, thereby reducing the optical purity of the product and/or substrate. Also, with moderately polar alcohol substrates, the alcohol itself often has appreciable water solubility, thus leading to potential contamination problems and corresponding reduced optical purities.

Other examples using cyclic anhydrides as enzymatic acylation agents but are not directed toward facilitating separation include Fukusaki et al., *Tetrahedron*, 1991, 47, 6223, and Yanamoto, et al., *Tetrahedron Lett.*, 1988, 29, 1717.

Thus, alternative methods for the separation of alcohols from the enantiomeric esters derived from enzymatic resolutions, in the greater context of alcohol purification, are needed.

SUMMARY OF THE INVENTION

The problem noted above has been solved with the discovery of a method for the purification of an alcohol comprising the sequential steps of (a) contacting an organic solution comprising an organic-soluble impurity and a crude parent alcohol with a cyclic anhydride to form a mixture comprising a corresponding alcohol half-ester and said organic-soluble impurity wherein said half-ester substituent is derived from the cyclic anhydride; (b) combining said mixture with a base in an aqueous environment wherein said half-ester forms a water-soluble salt; (c) separating said water soluble salt from said organic-soluble impurity; and (d) removing said half-ester substituent from said water-soluble salt to afford a purified parent alcohol.

This invention may be utilized in the purification of many alcohols from inert impurities that are organic-soluble but does not apply for impurities which are water-soluble (at any pH between 0 and 14), since separation of these types of impurities can be effected by a simple aqueous extraction. The method is particularly useful in the separation of enzymatic resolution product mixtures. The purification is non-chromatographic and the enantiomeric integrity of the products is maintained.

DETAILED DESCRIPTION

According to the invention, a purification system has been discovered to separate alcohols from organic-soluble impurities. In order to operate most efficiently, the impurities should be inert to cyclic anhydride acylating conditions. Although the solution containing the crude alcohol and the organic-soluble impurity may contain insoluble impurities, the separation of the insoluble impurities is easily accomplished by techniques well-known to those skilled in the art.

The crude alcohol solution to be purified by the inventive method is defined to include cyclic, heterocylic or heteroaromatic (wherein the hetero atom is selected from oxygen, sulfur, or nitrogen), aromatic, straight or branched aliphatic (including primary, secondary, or tertiary) chiral or achiral alcohols to be separated from an impurity. Preferably, the alcohol to be purified is defined by the formula $R^1OH$ wherein $R^1$ represents an unsubstituted or substituted, straight or branched $C_1$–$C_{20}$ alkyl, $C_3$–$C_{20}$ cycloalkyl, heterocylic, or cycloalkenyl, $C_8$–$C_{20}$ cycloalkynyl, $C_2$–$C_{20}$ alkenyl, $C_2$–$C_{20}$ alkynyl group, or an unsubstituted or substituted $C_4$–$C_{20}$ aromatic or heteroaromatic group (with said substituents designated above selected from one or more of the following: a halogen, a cyano, a $C_1$–$C_{20}$ alkyl, a $C_2$–$C_{20}$ alkenyl, a $C_4$–$C_{20}$ aromatic, a $C_1$–$C_{20}$ ether, a $C_1$–$C_{20}$ ester, a $C_1$–$C_{20}$ sulfonate ester, a nitro, a $C_1$–$C_{20}$ ketone, or a $C_1$–$C_{20}$ thioether group, and said hetero atom(s) selected from oxygen, sulfur, or nitrogen). Preferably the impurity to be separated from the alcohol is an alcohol derivative thereof. More preferably, the crude alcohol solution constitutes a mixture resulting from an enzymatic resolution containing a chiral alcohol and its corresponding antipodal alcohol derivative (treated as the organic soluble impurity). The mixture may be derived from an enzymatic acylation, hydrolysis, or some other reaction affording a mixture of a free alcohol and an alcohol derivative (where the derivative is inert to acylating conditions) as shown in Scheme I below, where X is, for example, a non-ionizable acyl moiety.

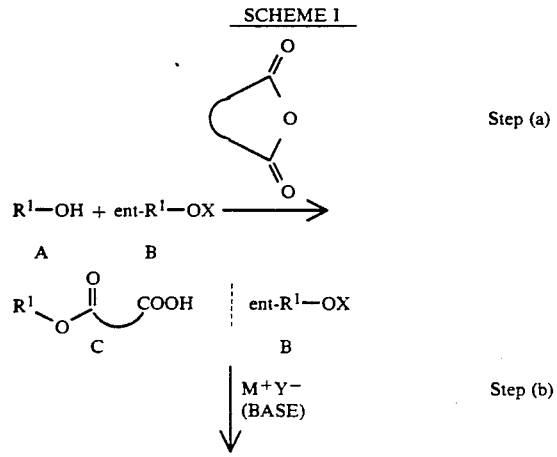

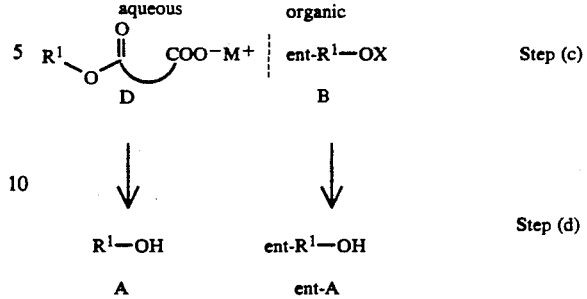

As shown in Scheme I for a chiral alcohol and the enantiomeric derivative, the free alcohol (A) of the mixture of alcohol and corresponding alcohol derivative (B) is acylated with a cyclic anhydride (represented generically) affording the corresponding half-ester of the alcohol (C) and the unreacted alcohol derivative (B) from the original mixture in solution. The half-ester of the alcohol then forms a water-soluble salt (D) when contacted with a base. To take advantage of the water-solubility of the salt, water must be present to facilitate separation of the salt from an organic solution of the organic-soluble unreacted alcohol derivative (B). After separation of the water soluble salt (D) from the unreacted alcohol derivative (B), via the water-solubility/organic-solubility distinction, the half-ester substituent may be removed from the salt through known techniques to afford the purified alcohol (A). In the case where the alcohol and alcohol derivative (ester) are products of an enzymatic kinetic resolution, the separated chiral alcohol can be obtained without substantial loss of optical purity. Also, in these cases, the organic-soluble ester (alcohol derivative) may often be reacted through known techniques, to afford the antipodal alcohol (ent-A). An advantage of this method is that the optical purities of the alcohol and alcohol derivative are substantially maintained.

Most preferably, the crude alcohol solution comprises a chiral alcohol to be separated from the corresponding enantiomeric antipodal ester (the "impurity") wherein the alcohol is represented by $R^1OH$ where $R^1$ is 1-phenylethyl, 1-phenyl-2-propyl, 1-phenyl-3-butyl, 1-phenylthio-3-butyl, 1-phenoxy-2-propyl, 1-adamantylethyl, 1-tosyloxy-3-buten-2-yl, 2-tert-butoxy- 3-buten-1-yl, 2-phenoxy-3-buten-1-yl, trans-2-phenylcyclohexyl, and trans-2-acetoxycyclopentyl.

According to the invention, the alcohol and impurity are in an organic solution. Organic solvents that may be employed for this purpose include, for example, aliphatic and aromatic hydrocarbons, ethers, esters, ketones, and halogenated hydrocarbons which are largely immiscible with water, e.g., dichloromethane, diethylether, tert-butyl methyl ether, ethyl acetate, hexane, toluene, etc.

Any suitable cyclic anhydride may be reacted with the crude alcohol solution. Preferably the anhydride is a $C_2$–$C_{20}$ substituted or unsubstituted cyclic anhydride and mixtures thereof, wherein the substituents may be $C_1$–$C_{20}$ alkyl, alkenyl, ether, thioether, alkylhalide, or halide(s). More preferably employed as the cyclic anhydride is a succinic, phthalic, or maleic anhydride. For purposes of availability and cost, succinic anhydride is the most preferred cyclic anhydride.

According to step (b) of the invention, the base reacts with the acid substituent of the alcohol half-ester to generate a water-soluble salt. Suitable bases that may be used include aqueous and nonaqueous bases, with the conjugate acid of the bases having a pKa of from 7 to 25, with the stronger bases preferably used in a lesser amount. More preferably the conjugate acid of the base has a pKa of from 7 to 14, include such bases as KOH, NaOH, $K_2CO_3$, $Na_2CO_3$, $KHCO_3$, $NaHCO_3$, and mixtures thereof. More preferably employed as the base are aqueous solutions of $KHCO_3$ or $NaHCO_3$. As previously indicated herein, water must be present to create an aqueous environment prior to step (c) to facilitate separation of the water-soluble salt and unreacted organic-soluble impurity. One convenient method of creating an aqueous environment is to employ the base in an aqueous solution, although water may be included as a separate component. The base must present in an amount sufficient to deprotonate the alcohol half-ester and thereby ionize it to afford water solubility. Preferably, about 1 equivalent to large excess of the base may be used.

According to the invention in step (c) the water-soluble salt is separated from the organic-soluble impurity(ies). This separation may be accomplished by any of the known techniques for separating aqueous and organic solutions.

The alcohol half-ester substituent may be isolated from the aqueous extraction solution by any number of techniques including, for example, acidification with an acid to pH<about 3 and extraction with organic solvent. The desired alcohol can then be regenerated from the half ester (step d) by extended treatment of the cyclic anhydride half ester by any number of techniques, including, for example, treatment with acid or base, preferably with either a strong aqueous base with the conjugate acid of the base having a pKa of $\geq 12$ (caustic) or strong mineral acid having a pKa of $\leq 1$ (e.g., HCl). Alternatively, in many circumstances, the water-soluble salt need not be isolated and the half-ester substituent can be cleaved while in the aqueous extraction media by the addition of a strong base such as caustic after step (c) (extraction) of the inventive method, thus eliminating the need for an isolation step.

As described previously, the inventive method is particularly useful when used in conjunction with enzymatic resolutions because the inventive purification scheme may easily be included as a step in the resolution process. An advantage of the invention is that because it is independent from the resolution, it is compatible with a wide selection of enzymes that may be used in the resolution process and the resolution is not limited to enzymatic esterification. Additionally, the optical purities of both the chiral alcohol and the enantiomeric ester are substantially maintained during the separation. This maintenance of the optical purity may be measured by a degree of enantiomeric excess ("ee") present for each compound.

For enzymatic resolution protocols where a chiral alcohol and corresponding antipodal ester are separated, maintaining the optical purity of the various species during the separation sequence is dependent on ensuring that none of the organic soluble ester is present in the aqueous extracts. Unlike other solubility of the ester can be manipulated by engineering the hydrophobicity of the ester (e.g., by changing the chain length).

The following examples illustrate the invention, but it is understood that the invention is not limited thereto.

EXAMPLES

The reaction scheme shown below represents the general method illustrated by the examples. In the examples, a mixture is separated, where $R^1OH$ represents an alcohol and ent-$R^1$—OCOX represents a corresponding antipodal ester. The various substituents as represented by $R^1$ are shown structurally as letters a-n following the reaction scheme hereinafter. The X of the ent-$R^1$—OCOX was either a —$CH_3$ group or a —$CH_2Cl$ group, as described in each individual example. Either succinic, phthalic, or maleic anhydride was used as the cyclic anhydride. $Et_3N$ represents triethylamine and cat/DMAP represents 4-N,N-dimethylaminopyridine used in catalytic amounts.

As shown in the Scheme II, the mixture of alcohol and enantiomeric ester was first treated with the cyclic anhydride under standard acylation conditions in an inert organic solvent. The second step involved extraction of the organic solution with aqueous base to deprotonate the diacid half-ester of the alcohol and separate it (aqueous) from the enantiomeric ester (organic). In the final step, the parent alcohol can often be regenerated from each piece, usually by treatment with either strong base or strong acid.

SCHEME II
GENERAL REACTION SCHEME FOR EXAMPLES

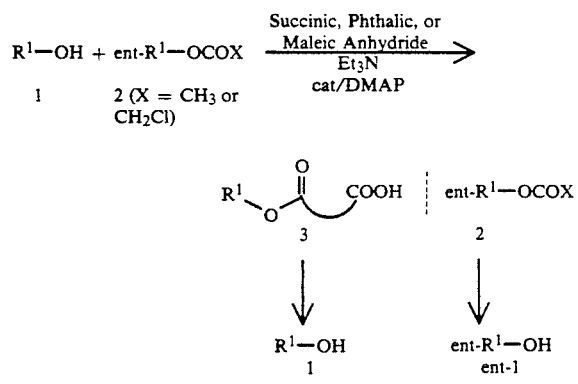

ALCOHOL/ESTER PAIRS FOR EXAMPLES ($R^1$ = a-n)

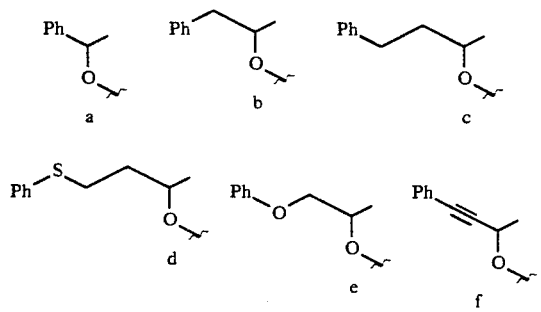

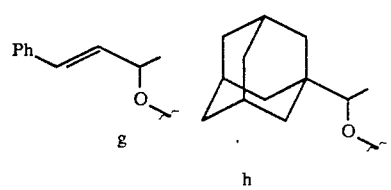

-continued
SCHEME II

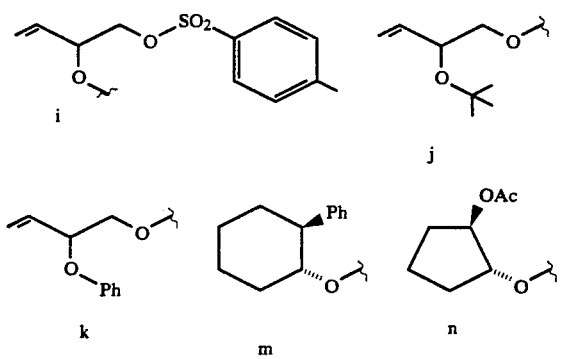

Example 1

1-Phenylethanol Substrate (1a)

Alcohol 1a (1.21 ml; 10 mmol) was dissolved in tert-butyl methyl ether (20 mL) and treated with vinyl acetate (2.77 mL; 30 mmol; 3 equiv.) and lipase SAM-II ™ (derived from *Pseudomonas fluorescens* 200 mg; Amano International Enzyme Co.). The mixture was stirred for 24 h until $^1$H nmr analysis indicated approximately 50% conversion to acetate 2a. The enzyme was removed by filtration and the filtrate was concentrated to afford a mixture of S-1a and R-2a (1.43 g).

The mixture of S-1a and R-2a (approximately 5 mmol each) was dissolved in dichloromethane (DCM) (5 mL) and treated with triethylamine (1.05 mL; 7.5 mmol; 1.5 equiv.) and 4-N,N-dimethylaminopyridine (DMAP; 6 mg; 0.05 mmol; 0.01 equiv.). The mixture was treated with succinic anhydride (525 mg; 5.25 mmol; 1.05 equiv.) and stirred at room temperature to completely consume 1a (tlc analysis). The reaction mixture was diluted with 1:1 ethyl acetate:hexanes (30 mL) and extracted with saturated aqueous NaHCO$_3$ (3×10 mL). The organic solution was concentrated and the residue was diluted with hexanes (30 mL), extracted with saturated NaHCO$_3$ (2×10 mL), dried (MgSO$_4$) and concentrated to afford R-2a (672 mg; 82%) $^1$H nmr (300 MHz, CDCl$_3$): 7.361–7.259 (5H, m); 5.881 (1H, q, J=6.6 Hz); 2.073 (3H, s); 1.547 (3H, t, J=6.6 Hz). IR (neat film, cm$^{-1}$): 3000 (m); 1790 (s). EIMS (m/e): 164 (M+).

The combined aqueous extracts were acidified to pH 1 with HCl and extracted with dichloromethane (2×15 mL) and ethyl acetate (2×15 mL). The combined extracts were dried (MgSO$_4$) and concentrated to afford succinate half-ester S-3a, 1.05 g (95%).$^1$H nmr (300 MHz, CDCl$_3$): 7.351–7.261 (5H, m); 5.901 (1H, q, J=6.6 Hz); 2.700–2.612 (5H, m); 1.539 (3H, d, J=6.6 Hz). IR (neat film, cm$^{-1}$): 3000 (s); 1740 (s). EIMS (m/e): 222 (M+).

This half-ester S-3a (222 mg; 1.0 mmol) was dissolved in methanol (3 mL) and treated with potassium carbonate (276 mg; 2 mmol; 2 equiv.) and stirred overnight to completely consume 3a (tlc analysis). The reaction mixture was diluted with water (25 mL) and extracted with ether (2×10 mL). The combined extracts were dried (MgSO$_4$) and concentrated to afford 100 mg (82%) of S-1a. $^1$H nmr (300 MHz, CDCl$_3$): 7.375–7.257 (5H,m); 4.907 (1H, q, J=6.3 Hz); 1.850–1.700 (1H, m); 1.506 (3H, d, J=13.28 Hz). IR (neat film, cm$^{-1}$): 3400 (s); 2950 (s). $[\alpha]_D^{20}$ −39.9° (c. 1.455, CH$_3$OH). The absolute configuration of 1a is known to be S-(−) (commercially available from Aldrich Chemical Co.). $^1$H nmr analysis of the MTPA ester using an analogous procedure to that of Dale et al., *J. Org. Chem.*, 1969, 34, 2543, indicated 92% ee for S-1a.

The acetate R-2a (164 mg; 1.0 mmol) was deacetylated by overnight treatment with potassium carbonate (276 mg; 2.0 mmol; 2 equiv.) in methanol (3 mL). The product R-1a (89 mg; 73%) was isolated by dilution with water (25 mL), extraction with ether (2×10 mL), drying of the extracts (MgSO$_4$), and concentration. All achiral properties of 1a are as reported above. $^1$H nmr analysis of the MTPA ester using an analogous procedure to that of Dale et al., *J. Org. Chem.*, 1969, 34, 2543, indicated 90% ee for R-1a. $[\alpha]_D^{20}$+40.3° (c. 1.06, CH$_3$OH).

Example 2

1-Phenyl-2-propanol Substrate (1b)

1-Phenyl-2-propanol (1b) (3.5 mL; 25 mmol) was dissolved in DCM (25 mL). Triethylamine (5.21 mL; 37.5 mmol; 1.5 equiv.) was added followed by DMAP (153 mg; 1.25 mmol; 0.05 equiv.). The reaction mixture was cooled to 0° and acetic anhydride (2.83 mL; 30 mmol; 1.2 equiv.) was added. The reaction mixture was allowed to warm slowly to room temperature overnight to completely consume 1b (tlc analysis). The reaction mixture was diluted with 50 mL of 1:1 ether:hexanes and washed with water (25 mL), 1N HCl (2×25 mL), and saturated NaHCO$_3$ (25 mL). The organic layer was dried (MgSO$_4$) and concentrated to afford 4.67 g (99%) of crude 2b which was used as is. $^1$H nmr (300 MHz, CDCl$_3$): 7.35–7.15 (5H, m); 5.12 (1H, m(6), J=6.5 Hz); 2.927 (1H, dd, J=6.68, 13.56 Hz); 2.748 (1H, dd, J=6.53, 13.64 Hz); 1.996 (3H, s); 1.215 (3H, d, J=6.25 Hz). IR (neat film, cm$^{-1}$): 3000 (b); 1790 (s).

Acetate 2b (1.77 g; 10 mmol) was combined with pH 7 phosphate buffer (25 g) and the pH was adjusted to 7.00. Lipase SAM-II (400 mg; Amano International Enzyme Co.) was added and hydrolysis commenced. The reaction was kept at constant pH by automatic titration with 1.000N NaOH and conversion was followed by base uptake. After approximately 45% conversion the reaction was halted by extraction with ether (3×20 mL). The extracts were dried (MgSO$_4$) and concentrated to afford 1.268 g of the mixture of R-1b and S-2b.

The mixture of R-1b and S-2b (approximately 3 mmol each) was dissolved in dichloromethane (5 mL) and treated with triethylamine (0.63 mL; 4.5 mmol; 1.5 equiv.) and DMAP (4 mg; 0.03 mmol; 0.01 equiv.) and cooled to 0°. The resulting solution was treated with succinic anhydride (330 mg; 3.3 mmol; 1.1 equiv.) and stirred overnight at room temperature to completely consume 1b (tlc analysis). The reaction mixture was diluted with ether (30 mL) and extracted with saturated aqueous NaHCO$_3$ (3×10 mL). The organic solution was dried (MgSO$_4$) and concentrated to afford S-2b (578 mg; >99%). All achiral properties of 2b are as reported above.

The combined aqueous extracts were acidified to pH 1 with HCl and extracted with DCM (2×15 mL) and ether (2×15 mL). The combined extracts were dried (MgSO$_4$) and concentrated to afford succinate half-ester R-3b, 626 mg (88 %). $^1$H nmr (300 MHz, CDCl$_3$): 7.308–7.172 (5H, m); 5.131 (1H, m(6), J=6.4 Hz); 2.926 (1H, dd, J=6.75, 13.64 Hz); 2.760 (1H, dd, J=6.50, 13.65 Hz); 2.684–2.533 (4H, m); 1.221 (3H, d, J=6.22

Hz). IR (neat film, cm$^{-1}$): 3000 (s); 1750 (s). FDMS (m/e): 237 (MH+).

This half-ester R-3b (236 mg; 1.0 mmol) was dissolved in methanol (2 mL) and treated with potassium carbonate (276 mg; 2.0 mmol; 2 equiv.) and stirred overnight to completely consume 3b (tlc analysis). The reaction mixture was diluted with water and extracted with ether (3×10 mL). The combined extracts were dried (MgSO$_4$) and concentrated to afford 96 mg (71%) of R-1b. $^1$H nmr (300 MHz, CDCl$_3$): 7.346–7.205 (5H, m); 4.11–3.95 (1H, m); 2.802 (1H, dd, J=4.84, 13.46 Hz); 2.692 (1H, dd, J=5.43, 13.40 Hz); 1.565 (1H, s); 1.255 (3H, d, J=5.72 Hz). IR (neat film, cm$^{-1}$): 3350 (b); 2900 (m); 1730 (m). [α]$_D^{20}$ −20.5° (c. 1.01, CH$_3$OH). The absolute configuration of 1b is known to be S-(+) (Schmidt et al., *Chem. Ber.* 1980, 113, 1691). $^1$H nmr analysis of the MTPA ester using an analogous procedure to that of Dale et al., *J. Org. Chem.*, 1969, 34, 2543, indicated 90% ee for R-1b.

The acetate S-2b (177 mg; 1.0 mmol) was deacetylated by overnight treatment with potassium carbonate (276 mg; 2.0 mmol; 2 equiv.) in methanol (2 mL). The product S-1b (108 mg; 79%) was isolated by dilution with water (25 mL), extraction with ether (3×10 mL), drying of the extracts (MgSO$_4$), and concentration. All achiral properties of 1b are as reported above. $^1$H nmr analysis of the MTPA ester using an analogous procedure to that of Dale et al., *J. Org. Chem.*, 1969, 34, 2543, indicated 70% ee for S-1b. [α]$_D^{20}$ +15.0° (c. 1.05, CH$_3$OH).

Example 3

4-Phenyl-2-butanol (1c)

Benzylacetone (7.5 mL, 50 mmol) was dissolved in ethanol (50 mL) and cooled to 0° C. Sodium borohydride (1.89 g, 50 mmol, 1 equiv.) was added. The mixture was stirred and allowed to warm to room temperature overnight. All of the starting material was gone by tlc analysis, so the mixture was poured into water (50 mL) and ether (50 mL). The layers were separated and the aqueous layer was extracted with ether (2×25 mL). The organic layers were combined and concentrated. The resulting aqueous residue was poured into ether (50 mL). The organic layer was removed, dried (MgSO$_4$), and concentrated to provide 1c (6.86 g; 91%). $^1$H nmr (300 MHz, CDCl$_3$): 7.38–7.15 (5H, m); 3.85 (1H, m(6), J=6.17 Hz); 2.82–2.61 (2H, m); 1.79 (2H, q, J=7.12 Hz); 1.421 (1H, s); 1.236 (3H, d, J=6.09 Hz). IR (neat film, cm$^{-1}$): 3250 (b); 2900 (b). EIMS (m/e): 150 (M+).

The racemic alcohol 1c (3.0 g; 20 mmol) was dissolved in 20 mL DCM. Triethylamine (4.18 mL; 30 mmol; 1.5 equiv.) and DMAP (122 mg; 1.0 mmol; 0.05 equiv.) were added and the mixture was cooled to 0° C. Acetic anhydride (2.26 mL; 24 mmol; 1.2 equiv.) was added and the mixture was allowed to warm to room temperature overnight. The mixture showed no starting material by tlc analysis, and was poured into ether, washed with water, 1N HCl, and saturated sodium bicarbonate. The organic layer was dried (MgSO$_4$) and concentrated to afford 3.81 g (99%) of 2c. $^1$H nmr (300 MHz, CDCl$_3$): 7.31–7.16 (5H, m); 4.92 (1H, m(6), J=4.94 Hz); 2.65 (2H, m); 2.035 (3H, s); 1.9–1.7 (2H, m); 1.253 (3H, d, J=6.3 Hz). IR (neat film, cm$^{-1}$): 2800 (b); 1730 (s).

The acetate 2c (1.92 g; 10 mmol) was added to pH 7 phosphate buffer (25 mL) and the pH was adjusted to 7.00. The enzyme, lipase SAM-II (100 mg; Amano International Enzyme Co.), was added. An automatic titrator was used to maintain pH 7.00 by the addition of 1.000N NaOH. The amount of NaOH consumed was a convenient measure of conversion. At approximately 50% conversion, the mixture was extracted with ether (3×20 ml), dried (MgSO$_4$), and concentrated to afford 1.49 g of the mixture of R-1c and S-2c.

The mixture of R-1c and S-2c (approximately 1.5 mmol each) was dissolved in dichloromethane (3 mL) and treated with triethylamine (314 mL; 2.25 mmol; 1.5 equiv.) and DMAP (2 mg; 0.015 mmol; 0.01 equiv.) and cooled to 0°. The resulting solution was treated with succinic anhydride (165 mg; 1.65 mmol; 1.1 equiv.) and stirred at room temperature to completely consume 1c (tlc analysis). The reaction mixture was diluted with ether (30 mL) and extracted with saturated aqueous NaHCO$_3$ (3×15 mL). The organic solution was dried (MgSO$_4$) and concentrated to afford S-2c (236 mg; 82%).

The combined aqueous extracts were acidified to pH 1 with HCl and extracted with DCM (2×10 mL) and ethyl acetate (2×10 mL). The combined extracts were dried (MgSO$_4$) and concentrated to afford succinate half-ester R-3c, 394 mg (>99%). $^1$H nmr (300 MHz, CDCl$_3$): 7.308–7.159 (5H, m); 4.936 (1H, m(6), J=6.4 Hz); 2.731–2.558 (6H, m); 1.996–1.741 (2H, m); 1.250 (3H, d, J=6.2 Hz). IR (neat film, cm$^{-1}$): 3000 (s); 1750 (s). FDMS (m/e): 250 (M+).

This half-ester R-3c (250 mg; 1.0 mmol) was dissolved in methanol (2 mL) and treated with potassium carbonate (276 mg; 2.0 mmol; 2 equiv.) and stirred overnight to completely consume 3c (tlc analysis). The reaction mixture was diluted with water (25 mL) and extracted with ether (3×10 mL). The combined extracts were dried (MgSO$_4$) and concentrated to afford 118 mg (79%) of R-1c. All achiral properties of 1c are as reported above. The absolute configuration of 1c was not exhaustively proven, but was presumed to be R-(−) by analogy with the enzymatic results of 1a and 1b. $^1$H nmr analysis of the MTPA ester using an analogous procedure to that of Dale et al., *J. Org. Chem.*, 1969, 34, 2543, indicated 54% ee for R-1c. [α]$_D^{20}$ −8.2° (c. 1.19, CH$_3$OH).

The acetate S-2c (192 mg; 1.0 mmol) was deacetylated by overnight treatment with potassium carbonate (276 mg; 2.0 mmol; 2 equiv.) in methanol (2 mL). The product S-1c (148 mg; 99%) was isolated by dilution with water (25 mL), extraction with ether (3×10 mL), drying of the extracts (MgSO$_4$), and concentration. All achiral properties of 1c are as reported above. $^1$H nmr analysis of the MTPA ester using an analogous procedure to that of Dale et al., *J. Org. Chem.*, 1969, 34, 2543, indicated 48% ee for S-1c. [α]$_D^{20}$ +13.2° (c. 1.125, CH$_3$OH).

Example 4

4-Phenylthio-2-butanol (1d)

Racemic 4-phenylthio-2 butanol (1.82 g; 10 mmol) was dissolved in t-butyl methyl ether (20 ml). Vinyl acetate (2.76 mL; 30 mmol, 3 equiv.) and the enzyme, Lipase SAM-II (200 mg; Amano International Enzyme Co.), were added. The reaction was monitored by periodic removal of aliquots followed by $^1$H nmr analysis. After 2 days the reaction had reached 50% conversion, and the mixture was filtered, the precipitate was washed with ether, and the filtrate was concentrated to afford 1.83 g of the mixture of S-1d and R-2d.

The mixture of S-1d and R-2d (approximately 1.5 mmol each) was dissolved in dichloromethane (3 mL) and treated with triethylamine (314 mL; 2.25 mmol; 1.5 equiv.) and DMAP (2 mg; 0.015 mmol; 0.01 equiv.) and cooled to 0°. The mixture was treated with succinic anhydride (210 mg; 2.1 mmol; 1.4 equiv.) and stirred at room temperature to completely consume 1d (tlc analysis). The reaction mixture was diluted with ether (30 mL) and extracted with saturated aqueous $NaHCO_3$ (3×15 mL). The organic solution was dried ($MgSO_4$) and concentrated to afford R-2d (329 mg; 98%) $^1H$ nmr (300 MHz, $CDCl_3$): 7.351–7.186 (5H, m); 5.020 (1H, m(6), J=6.44 Hz); 3.02–2.86 (2H, m); 2.036 (3H, s); 1.943–1.805 (2H, m); 1.235 (3H, d, J=6.29 Hz). IR (neat film, $cm^{-1}$): 3000 (m); 1750 (s).

The combined aqueous extracts were acidified to pH 1 with HCl and extracted with DCM (2×10 mL) and ethyl acetate (2×10 mL). The combined extracts were dried ($MgSO_4$) and concentrated to afford succinate half-ester S-3d, 377 mg (89 %). $^1H$ nmr (300 MHz, $CDCl_3$): 7.4–7.1 (5H, m); 5.07 (1H, m); 2.95 (2H, m); 2.684 (2H, m); 2.592 (2H, m); 1.9 (2H, m); 1.231 (3H, d, J=6.30 Hz). IR (neat film, $cm^{-1}$): 3450 (s); 2300 (w); 1600 (m). FDMS (m/e): 282 ($M^+$).

This half-ester S-3d (282 mg; 1.0 mmol) was dissolved in methanol (3 mL) and treated with potassium carbonate (276 mg; 2.0 mmol; 2 equiv.) and stirred overnight to completely consume 3 (tlc analysis). The reaction mixture was diluted with water (25 mL) and extracted with ether (3×10 mL). The combined extracts were dried ($MgSO_4$) and concentrated to afford 151 mg (83%) of S-1d. $^1H$ nmr (300 MHz, $CDCl_3$): 7.358–7.177 (5H, m); 3.97 (1H, m(6), J=6.17 Hz); 3.03 (2H, m(8), J=7.1 Hz); 1.76 (2H, q, J=6.5 Hz); 1.558 (1H, s); 1.218 (3H, d, J=6.28 Hz). IR (neat film, $cm^{-1}$): 3400 (b); 2900 (s); 1680 (s). $[\alpha]_D^{20}$ +31.4° (c. 1.02, $CH_3OH$). The absolute configuration of 1d was determined to be S-(+) by oxidation to the corresponding sulfone, whose absolute configuration was proven by independent synthesis. $^1H$ nmr analysis of the MTPA ester using an analogous procedure to that of Dale et al., *J. Org. Chem.*, 1969, 34, 2543, indicated 82% ee for S-1d.

The acetate R-2d (224 mg; 1.0 mmol) was deacetylated by overnight treatment with potassium carbonate (276 mg; 2.0 mmol; 2 equiv.) in methanol (3 mL). The product R-1 (179 mg; 98%) was isolated by dilution with water (25 mL), extraction with ether (3×10 mL), drying of the extracts ($MgSO_4$), and concentration. All achiral properties of 1d are as reported above. $^1H$ nmr analysis of the MTPA ester using an analogous procedure to that of Dale et al., *J. Org. Chem.*, 1969, 34, 2543, indicated 72% ee for R-1d. $[\alpha]_D^{20}$ −18.9° (c. 1.005, $CH_3OH$).

Example 5

1-Phenoxy-2-propanol (1e)

Phenoxy-2-propanone (3.4 mL, 25 mmol) was dissolved in ethanol (30 mL) and cooled to 0° C. Sodium borohydride (0.95 g; 25 mmol; 1 equiv.) was added. The mixture was stirred and allowed to warm to room temperature overnight. All of the starting material was gone according to tlc analysis, so the mixture was poured into water (30 mL) and ether (30 mL). The layers were separated and the aqueous layer was extracted with ether (2×20 mL). The organic layers were combined and concentrated. The resulting aqueous residue was poured into ether (25 mL). The organic layer was removed, dried ($MgSO_4$), and concentrated to provide 1e (3.2 g; 85%). $^1H$ nmr (300 MHz, $CDCl_3$): 7.332–7.261 (3H, m); 6.995–6.904 (2H, m); 4.15–4.24 (1H, m); 3.972–3.768 (2H, m); 1.559 (1H, s); 1.290 (3H, d, J=6.38 Hz). IR (neat film, $cm^{-1}$): 3350 (b, s); 2900 (s); 1590 (m). EIMS (m/e): 152 ($M^+$).

The alcohol 1e (1.52 g; 10 mmol) was dissolved in t-butyl methyl ether (20 ml). Vinyl acetate (2.76 mL; 30 mmol, 3 equiv.) and the enzyme, Lipase SAM-II 200 mg; Amano International Enzyme Co.), were added. The reaction was monitored by periodic removal of aliquots followed by $^1H$ nmr analysis. When the reaction had reached 50% conversion (17 h) the mixture was filtered, the precipitate was washed with ether, and the filtrate was concentrated to afford a mixture of S-1e and R-2e (1.58 g).

The mixture of S-1e and R-2e (519 mg; approximately 1.5 mmol each) was dissolved in dichloromethane (3 mL) and treated with triethylamine (314 mL; 2.25 mmol; 1.5 equiv.) and DMAP (20 mg; 0.15 mmol; 0.1 equiv.) and cooled to 0°. The mixture was treated with succinic anhydride (225 mg; 2.25 mmol; 1.5 equiv.) and stirred at room temperature to completely consume 1e (tlc analysis). The reaction mixture was diluted with ether (30 mL) and extracted with saturated aqueous $NaHCO_3$ (3×10 mL). The organic solution was dried ($MgSO_4$) and concentrated to afford R-2e (358 mg; >99%) $^1H$ nmr (300 MHz, $CDCl_3$): 7.33–7.22 (2H, m); 7.01–6.85 (3H, m); 5.32–5.18 (1H, m); 4.08–3.91 (2H, m); 2.068 (3H, s); 1.363 (3H, d, J=6.4 Hz). IR (neat film, $cm^{-1}$): 3000 (w, b); 1740 (s); 1600 (s). EIMS (m/e): 194 ($M^+$).

The combined aqueous extracts were acidified to pH 1 with HCl and extracted with DCM (2×10 mL) and ether (2×10 mL). The combined extracts were dried ($MgSO_4$) and concentrated to afford succinate half-ester S-3e, 419 mg (>99%). $^1H$ nmr (300 MHz, $CDCl_3$): 7.4–6.8 (5H, m); 5.289 (1H, m(6), J=5.4 Hz); 4.023 (1H, dd, J=4.41, 10.41 Hz); 3.967 (1H, dd, J=4.81, 10.51 Hz); 2.709–2.579 (4H, m); 1.360 (3H, d, J=6.5 Hz). IR (neat film, $cm^{-1}$): 3000 (s); 1750 (s); 1600 (m). FDMS (m/e): 252 ($M^+$).

This half-ester S-3e (252 mg; 1.0 mmol) was dissolved in methanol (3 mL) and treated with potassium carbonate (276 mg; 2.0 mmol; 2 equiv.) and stirred overnight to completely consume 3e (tlc analysis). The reaction mixture was diluted with water (25 mL) and extracted with ether (3×10 mL). The combined extracts were dried ($MgSO_4$) and concentrated to afford 130 mg (86%) of S-1e. All achiral properties of 1e are as reported above. $[\alpha]_D^{20}$ +10.3° (c. 1.075, $CH_3OH$). The absolute configuration of 1e was inferred to be S-(+) by consideration of the overwhelming R-enantioselectivity of Lipase SAM-II (see substrates 1a, 1b, and 1d). $^1H$ nmr analysis of the MTPA ester using an analogous procedure to that of Dale et al., *J. Org. Chem.*, 1969, 34, 2543, indicated 74% ee for S-1e.

The acetate R-2e (194 mg; 1.0 mmol) was deacetylated by overnight treatment with potassium carbonate (276 mg; 2.0 mmol; 2 equiv.) in methanol (3 mL). The product R-1e (152 mg; 99%) was isolated by dilution with water (25 mL), extraction with ether (3×10 mL), drying of the extracts ($MgSO_4$), and concentration. All achiral properties of 1e are as reported above. $^1H$ nmr analysis of the MTPA ester using an analogous procedure to that of Dale et al., *J. Org. Chem.*, 1969, 34, 2543, indicated 90% ee for R-1e. $[\alpha]_D^{20}$ −6.8° (c. 1.075, $CH_3OH$).

Example 6

4-Phenyl-3-butyne-2-ol (1f)

Phenylacetylene (5.5 mL; 50 mmol) was dissolved in THF (40 mL) and cooled to −78°. A 1.35M solution of n-butyllithium in hexane (37 mL; 50 mmol; 1.0 equiv.) was added dropwise and the resulting mixture was stirred at −78° for 1 h. Acetaldehyde (2.8 mL; 50 mmol; 1.0 equiv.) was added and the reaction mixture was allowed to warm overnight to room temperature. The mixture was diluted with ether (50 mL) and washed with water (3×25 mL). The organic solution was dried (MgSO$_4$) and concentrated, and the crude product was distilled in vacuo, affording 3.4 g (47%) of 1f, bp 94° C./approximately 2 mm Hg. $^1$H nmr (300 MHz, CDCl$_3$): 7.444–7.261 (5H, m); 4.762 (1H, q, J=5 96 Hz); 1.972 (1H, s); 1.557 (3H, d, J=6.58 Hz). IR (neat film, cm$^{-1}$): 3400 (s); 1600 (w). FDMS (m/e): 146 (M+).

Molecular sieves powder (4A, 1.5 g) was slurried in hexanes (20 mL) and 1f (1.46 g; 10.0 mmol) and vinyl acetate (2.77 mL; 30 mmol; 3 equiv.) were added. Lipase AK from Pseudomonas sp. (750 mg; Amano International Enzyme Co.) was added and the reaction mixture was stirred for 6 h (approximately 50% conversion). The enzyme was removed by filtration and the filtrate was concentrated to afford the mixture of S-1f and R-2f (1.63 g).

The mixture of S-1f and R-2f (1.002 g; approximately 3 mmol each) was dissolved in DCM (5 mL) and treated with triethylamine (627 mL; 4.5 mmol; 1.5 equiv.) and DMAP (4 mg; 0.03 mmol; 0.01 equiv.) and cooled to 0°. The mixture was treated with succinic anhydride (330 mg; 3.3 mmol; 1.1 equiv.) and stirred at room temperature to completely consume 1f (tlc analysis). The reaction mixture was diluted with ether (25 mL) and extracted with saturated aqueous NaHCO$_3$ (3×10 mL). The organic solution was dried (MgSO$_4$) and concentrated to afford R-2f (677 mg; >99%) $^1$H nmr (300 MHz, CDCl$_3$): 7.456–7.261 (5H, m); 5.683 (1H, q, J=6.65 Hz); 2.108 (3H, s); 1.580 (3H, d, J=6.69 Hz). IR (neat film, cm$^{-1}$): 3400 (s); 3000 (w); 1750 (w); 1600 (w). FDMS (m/e): 188 (M+).

The combined aqueous extracts were acidified to pH 1 with HCl and extracted with ether (3×20 mL). The combined extracts were dried (MgSO$_4$) and concentrated to afford succinate half-ester S-3f, 692 mg (94%). $^1$H nmr (300 MHz, CDCl$_3$): 7.452–7.260 (5H, m); 5.710 (1H, q, J=6.64 Hz); 2.742–2.605 (4H, m); 1.582 (3H, d, J=6.66 Hz). IR (neat film, cm$^{-1}$): 3500 (s); 3000 (s); 1750 (s). FDMS (m/e): 246 (M$^{30}$).

This half-ester S-3f (492 mg; 2.0 mmol) was dissolved in methanol (3 mL) and treated with potassium carbonate (552 mg; 4.0 mmol; 2 equiv.) and stirred overnight to completely consume 3f (tlc analysis). The reaction mixture was diluted with water (25 mL) and extracted with ether (3×10 mL). The combined extracts were dried (MgSO$_4$) and concentrated to afford 257 mg (88%) of S-1f. All achiral properties of 1f are as reported above. The optical purity (96% ee) and absolute configuration of S-1f were determined according to literature procedure (Burgess and Jennings, J. Am. Chem. Soc. 1991, 113, 6129). [α]$_D$20 −23.9° (c. 0.49, CH$_3$OH).

The acetate R-2f (376 mg; 2.0 mmol) was deacetylated by overnight treatment with potassium carbonate (552 mg; 4.0 mmol; 2 equiv.) in methanol (3 mL). The product R-1f (264 mg; 90%) was isolated by dilution with water (3 mL), extraction with ether (3× 15 mL), drying of the extracts (MgSO$_4$), and concentration. All achiral properties of 1f are as reported above. The optical purity (88% ee) and absolute configuration of R-1f were determined according to literature procedure (Burgess and Jennings, J. Am. Chem. Soc. 1991, 113, 6129 ). [α]$_D$20 +27.0° (c. 0.545, CH$_3$OH).

Example 7

E-1-Phenyl-2-butene-3-ol (1 g)

E-Cinnamaldehyde (6.3 mL; 50 mmol) was dissolved in THF (20 mL) and cooled to −78°. An ethereal solution of methyllithium (1.2M; 42 mL; 50 mmol; 1.0 equiv.) was added and the reaction mixture was stirred at −78° to consume the aldehyde. The reaction mixture was diluted with ether (25 mL) and washed with water (3×15 mL). The organic solution was dried (MgSO$_4$) and concentrated to afford crude 1 g, which was filtered through a pad of silica gel and eluted with 1:1 ether:hexanes to afford 6.61 g (89%) of 1 g. $^1$H nmr (300 MHz, CDCl$_3$): 7.399–7.164 (5H, m); 6.574 (1H, d, J=15.7 Hz); 6.268 (1H, dd, J=6.34 Hz, 15.89 Hz); 4.499 (1H, m(5), J=5.8 Hz); 1.642 (1H, s); 1.380 (3H, d, J=6.41 Hz). IR (neat film, cm$^{-1}$): 3400 (s); 3400 (s). FDMS (m/e): 149 (M+).

4A Molecular sieves (0.5 g) and Lipase AK (330 mg) from Pseudomonas sp. (Amano International Enzyme Co.) were mixed in hexanes and treated with vinyl acetate (3.69 mL; 40 mmol; 4 equiv.) and alcohol 1 g (1.32 g; 10 mmol). The mixture was stirred for 7 h and the enzyme was removed by filtration. The filtrate was concentrated to afford a mixture of S-1g and R-2g (1.46 g).

The mixture of S-1g and R-2g (approximately 3 mmol each) was dissolved in DCM and treated with triethylamine (627 mL; 4.5 mmol; 1.5 equiv.) and DMAP (4 mg; 0.03 mmol; 0.1 equiv.). The resulting solution was treated with succinic anhydride (330 mg; 3.3 mmol; 1.1 equiv.) and stirred at room temperature to completely consume 1 g (tlc analysis). The reaction mixture was diluted with ether and extracted with saturated aqueous NaHCO$_3$ (3×10 mL). The organic solution was dried (MgSO$_4$) and concentrated to afford R-2g (707 mg; >99%). $^1$H nmr (300 MHz, CDCl$_3$): 7.394–7.243 (5H, m); 6.601 (1H, d, J=15.93 Hz); 6.187 (1H, dd, J=6.76 Hz, 15.98 Hz); 5.526 (1H, m(5), J=5.9 Hz); 2.078 (3H, s); 1.410 (3H, d, J=6.5 Hz). IR (neat film, cm$^{-1}$): 2900 (m); 1750 (m); 1600 (m).

The combined aqueous extracts were acidified to pH 1 with HCl and extracted with ether (2×15 mL) and DCM (15 mL). The combined extracts were dried (MgSO$_4$) and concentrated to afford succinate half-ester S-3g, 602 mg (86%). $^1$H nmr (300 MHz, CDCl$_3$): 7.387–7.127 (5H, m); 6.588 (1H, d, J=16 Hz); 6.180 (1H, dd, J=6.58 Hz, 15.94 Hz); 5.528 (1H, m(5), J=6.58 Hz); 3.013 (4H, m); 2.617 (4H, m); 1.396 (3H, d, J=6.47 Hz). IR (neat film, cm$^{-1}$): 3000 (s); 2600 (m); 1700 (s). FDMS (m/e): 248 (M+).

This half-ester S-3g (232 mg; 1.0 mmol) was dissolved in methanol (3 mL) and treated with potassium carbonate (276 mg; 2.0 mmol; 2 equiv.) and stirred overnight to completely consume 3g (tlc analysis). The reaction mixture was diluted with water and extracted with ether (3×10 mL). The combined extracts were dried (MgSO$_4$) and concentrated to afford 118 mg (89%) of S-1g. All achiral properties of 1 g are as reported above. The absolute configuration of 1 g has been determined according to Burgess and Jennings, J. Am. Chem. Soc. 1991, 113, 6129. $^1$H nmr analysis of the MTPA ester using an analogous procedure to that of Dale et al., *J. Org. Chem.*, 1969, 34, 2543, indicated 97% ee for S-1g. $[\alpha]_D^{20}$ −9.8° (c. 0.49, CH$_3$OH).

The acetate R-2g (174 mg; 1.0 mmol) was deacetylated by overnight treatment with potassium carbonate (276 mg; 2.0 mmol; 2 equiv.) in methanol (3 mL). The product R-1g (127 mg; 96%) was isolated by dilution with water (25 mL), extraction with ether (3×10 mL), drying of the extracts (MgSO$_4$), and concentration. All achiral properties of 1 g are as reported above. $^1$H nmr analysis of the MTPA ester using an analogous procedure to that of Dale et al., *J. Org. Chem.*, 1969, 34, 2543, indicated 80% ee for R-1g. $[\alpha]_D^{20}$ +13.8° (c. 0.53, CH$_3$OH).

Example 8

1-Adamantylethanol (1h)

1-Adamantylethanol (1.8 g; 10 mmol) was dissolved in DCM (5 mL). Triethylamine (2.08 mL; 15 mmol; 1.5 equiv.) and DMAP (61 mg; 0.5 mmol; 0.05 equiv.) were added and the reaction mixture was cooled to 0°. Chloroacetic anhydride (2.05 g; 12 mmol; 1.2 equiv.) was added and the reaction mixture was allowed to warm to room temperature to completely consume 1h. The reaction mixture was diluted with water (25 mL) and ether (25 mL), and the layers were separated. The organic layer was washed with 1N HCl (2×10 mL) and saturated NaHCO$_3$ (15 mL), dried (MgSO$_4$), and concentrated to afford 2.41 g (94%) of 2h'. $^1$H nmr (300 MHz, CDCl$_3$): 4.618 (1H, q, J=6.51 Hz); 4.058 (2H, m); 1.990 (3H, br s); 1.739–1.488 (12H, m); 1.149 (3H, d, J=6.51 Hz). IR (neat film, cm$^{-1}$): 2900 (s); 1750 (s); 1725 (s). FDMS (m/e): 256 (M+).

Ester 2h' (1.92 g; 7.5 mmol) was slurried in pH 7 phosphate buffer and the pH was adjusted to 7.00. Lipase SAM-II (400 mg; Amano International Enzyme Co.) was added and hydrolysis commenced. The reaction was performed under constant pH by the use of an automatic titrator and conversion was monitored by the uptake of 1.000NNaOH. After approximately 50% conversion the reaction was stopped by extraction with ether (3×15 mL). The combined extracts were dried (MgSO$_4$) and concentrated to afford the mixture of R-1h and S-2h' (1.5 g).

The mixture of R-1h and S-2h' (approximately 3 mmol each) was dissolved in DCM (15 mL) and treated with triethylamine (627 mL; 4.5 mmol; 1.5 equiv.) and DMAP (6 mg; 0.03 mmol; 0.01 equiv.). The mixture was treated with succinic anhydride (330 mg; 3.3 mmol; 1.1 equiv.) and stirred at room temperature to completely consume 1h (tlc analysis). The reaction mixture was diluted with ether (25 mL), washed with 1N HCl (10 mL), and extracted with saturated aqueous NaHCO$_3$ (3×10 mL). The organic solution was dried (MgSO$_4$) and concentrated to afford S-2h' (285 mg; 37%). All achiral properties of 2h' are as reported above.

The combined aqueous bicarbonate extracts were acidified to pH 1 with HCl and extracted with ether (3×10 mL). The combined extracts were dried (MgSO$_4$) and concentrated to afford succinate half-ester R-3h, 308 mg (37%). $^1$H nmr (300 MHz, CDCl$_3$): 4.555 (1H, q, J=6.51 Hz); 2.712–2.598 (4H, m); 1.972 (3H. br s); 1.8–1.35 (12H, m); 1.092 (3H, d, J=6.48 Hz). IR (neat film, cm$^{-1}$): 3400 (s); 2900 (s); 1750 (s). FDMS (m/e): 281 (M+).

This half-ester R-3h (280 mg; 1.0 mmol) was dissolved in 1:1 methanol:water and treated with 10% sodium hydroxide (0.8 mL; 2 mmol; 2 equiv.) and stirred overnight to completely consume 3h (tlc analysis). The reaction mixture was diluted with ether (25 mL) and washed with water (3×15 mL). The ethereal solution was dried (MgSO$_4$) and concentrated to afford 94 mg (52%) of R-1h. $^1$H nmr (300 MHz, CDCl$_3$): 3.285 (1H, q, J=6.43 Hz); 1.997 (3H, br s); 1.8–1.2 (12H, m); 1.100 (3H, d, J=6.42 Hz). IR (neat film, cm$^{-1}$): 3300 (s, b,); 2900 (s). $[\alpha]_D^{20}$ −3.2° (c. 1.285, i-PrOH). The absolute configuration of 1h was tentatively assigned R-(−) by analysis of the MTPA ester of 1h according to the method of Dale and Mosher, *J. Am. Chem. Soc.* 1973, 95, 512. $^1$H nmr analysis of the MTPA ester using an analogous procedure to that of Dale et al., *J. Org. Chem.*, 1969, 34, 2543, indicated 94% ee for R-1h.

The chloroacetate S-2h' (256 mg; 1.0 mmol) was dissolved in 1:1 methanol:water and treated with 10% aqueous sodium hydroxide (0.8 mL; 2 mmol; 2 equiv.) and stirred overnight to completely consume 2h' (tlc analysis). The reaction mixture was diluted with ether (25 mL) and washed with water (3×15 mL). The ethereal solution was dried (MgSO$_4$) and concentrated to afford 176 mg (98%) of S-1h. All achiral properties of 1h are as reported above. $^1$H nmr analysis of the MTPA ester using an analogous procedure to that of Dale et al., *J. Org. Chem.*, 1969, 34, 2543, indicated 96% ee for S-1h. $[\alpha]_D^{20}$ +2.0° (c. 1.075, i-PrOH).

Example 9

1-Tosyloxy-2-hydroxy-3-butene (1i)

In this example, anhydride derivatization was performed without isolation of the enzymatic esterification products.

1,2-Dihydroxy-3-butene (20.00 g; 0.227 mol; 1.05 equiv.) was dissolved in pyridine (200 mL). The reaction mixture was cooled in an ice bath and p-toluenesulfonyl chloride (p-TsCl) (41.11 g; 0.216 mol) was added in four portions over 30 min. After thorough mixing, the reaction mixture was placed at 4° C for 18 h, at which time tlc analysis indicated no p-TsCl. The mixture was concentrated to approximately half the original volume at reduced pressure from a 40° C. water bath and then diluted with ether (200 mL). The mixture was washed with water (100 mL), ice-cold 3N HCl until the washes remained acidic (2×100 mL), and saturated sodium bicarbonate (100 mL). After drying the organic solution (MgSO$_4$), the solvent was removed to afford 41.73 g of a 91:9 mixture ($^1$H nmr analysis) of 1i and the corresponding di-tosylate. The crude product solidified over several days at −20° C. It was recrystallized from methylene chloride (50 mL) by the addition of hexanes (100 mL) and chilling to −20° C. to afford two crops (total 33.33 g; 61%) of 1i which was pure by tlc analysis, mp 38°–44° C. $^1$H nmr (300 MHz, CDCl$_3$): 7.800 (2H, d, J=8.25 Hz); 7.356 (2H, d, J=8.19 Hz); 5.751 (1H, ddd, J=5.38, 10.46, 16.55 Hz); 5.378 (1H, br d, J=17.05 Hz); 5.247 (1H, br d, J=10.48 Hz); 4.396 (1H, m); 4.066 (1H, dd, 2.451 (3H, s); 2.276 (2H, d, J=4.50 Hz). IR (KBr, cm$^{-1}$): 3520 (s,b); 1650 (w); 1600 (s); 1350 (s); 1170 (s). Combustion Analysis: Calcd - C, 54.53; H, 5.82; N, 0. Found - C, 54.84; H, 5.86; N, <0.3.

Alcohol 1i (12.1 g; 50 mmol) was dissolved in TBME (25 mL) and treated with triethylamine (0.70 mL; 5 mmol; 0.1 equiv.) and stirred for 15 min. Vinyl acetate (13.9 mL; 150 mmol; 3 equiv.) and Lipase PS-30 (0.50 g) from *Pseudomonas cepacia* (Amano International Enzyme Co.) were added. The mixture was stirred for 22 h until $^1$H nmr analysis of an aliquot indicated 50% conversion to acetate 2i. The enzyme was removed by filtration and the filtrate containing a mixture of S-1i and R-2i was taken directly to the next step.

The TBME solution of S-1i and R-2i (approximately 25 mmol each) was treated with triethylamine (4.53 mL; 32.5 mmol 1.3 equiv.) and DMAP (305 mg; 2.5 mmol; 0.1 equiv.). The mixture was treated with succinic anhydride (2.75 g; 27.5 mmol; 1.1 equiv.) and stirred overnight at room temperature to completely consume 1i (tlc analysis). The reaction mixture was diluted with ether and water and the layers were separated. The organic layer was further extracted with saturated aqueous NaHCO$_3$ (2×10 mL). The organic solution was dried (MgSO$_4$) and concentrated to afford R-2i (7.46 g; '99%). $^1$H nmr (300 MHz, CDCl$_3$): 7.786 (2H, d, J=8.26 Hz); 7.355 (2H, d, J=8.03 Hz); 5.710 (1H, ddd, J=6.23, 10.54, 17.05 Hz); 5.396 (1H, m); 5.324 (1H, d, J=16.72 Hz); 5.279 (1H, d, J=10.63 Hz); 4.09 (2H, m); 2.453 (3H, s); 2.017 (3H, s). IR (neat film, cm$^{-1}$): 1740 (s); 1645 (w); 1600 (m); 1360 (s); 1175 (s).

The combined aqueous extracts were acidified to pH 1 with HCl and extracted with ethyl acetate (3×20 mL). The combined extracts were dried (MgSO$_4$) and concentrated to afford succinate half-ester S-3i, 8.65 g (>99 %). $^1$H nmr (300 MHz, CDCl$_3$): 8.9 (1H, br s); 7.767 (2H, d, J=8.20 Hz); 7.344 (2H, d, J=8.14 Hz); 5.690 (1H, ddd, J=6.08, 10.53, 16.91 Hz); 5.42 (1H, m); 5.314 (1H, d, J=18.07 Hz); 5.266 (1H, d, J=11.25 Hz); 4.113 (1H, dd, J=3.99, 10.95 Hz); 4.063 (1H, dd, J=6.35, 10.92 Hz); 2.6 (4H, m); 2.435 (3H, s). Combustion Analysis: Calcd: C, 52.62; H, 5.30; N, 0. Found: C, 52.37;

H, 5.18; N, <0.3.

Succinate half-ester S-3i (0.34 g; 1.0 mmol) was dissolved in methanol (1 mL) and water (0.67 mL) and 3M HCl (0.33 mL; 1.0 equiv.; 1.0 equiv.) was added. The reaction mixture was heated to 80° for 18 h to completely consume 3i according to tlc analysis. An aqueous workup afforded a mixture of 1i and dimethyl succinate. Recrystallization from ether by hexanes addition afforded 86 mg of S-3i (35%), which was >99.5% ee according to HPLC analysis on a CHIRALCEL OB ™ Column, 10% isopropanol in hexane eluent, 1.0 mL/min flow rate, λ=254 nm. All achiral properties of 1i are as reported above. The absolute configuration of 1i was determined by conversion to 3-butene-1,2-diol (of known configuration).

Acetate R-2i (7.46 g; 25 mmol) was dissolved in methanol (25 mL) and treated with concentrated HCl (1.0 mL; 12 mmol; 0.5 equiv.). The reaction mixture was stirred at room temperature for 2.5 d to completely consume 2i according to tlc analysis. The reaction mixture was neutralized with saturated aqueous NaHCO$_3$ and extracted with ethyl acetate (3×15 mL). The combined extracts were concentrated and the residue was diluted with ethyl acetate, dried (MgSO$_4$), and concentrated to afford 6.06 g (99%) of R-1i. All achiral properties of 1a are as reported above.

The following two examples utilize primary alcohols for the cyclic anhydride derivatization.

Example 10

1-Hydroxy-2-tert-butoxy-3-butene (1j)

Concentrated sulfuric acid (18M; 0.1 mL; 2 mmol; 0.02 equiv.) was added to 80 mL of tert-butanol. Butadiene monoepoxide (8.05 mL; 100 mmol) was added and the reaction mixture was heated to reflux overnight (15 h) to completely consume butadiene monoepoxide by GC analysis. The reaction mixture was concentrated at reduced pressure and the residue was dissolved in ether (40 mL) and washed with saturated aqueous NaHCO$_3$ (2×10 mL). The organic solution was dried (MgSO$_4$) and concentrated, and the crude product was fractionated in vacuo, affording pure 1j (3.12 g; 22%), bp 42°-45°/1 mm Hg along with an impure fraction, 3.83 g, bp 45°-85°/1 mm Hg. $^1$H nmr (300 MHz, CDCl$_3$): 5.797 (1H, ddd, J=6.29, 10.57, 17.07 Hz); 5.260 (1H, d, J=17.22 Hz); 5.144 (1H, d, J=10.50 Hz); 4.092 (1H, br q, J=5.76 Hz); 3.469 (1H, dd, J=4.45, 11.07 Hz); 3.399 (1H, dd, J=7.63, 11.14 Hz); 2.0 (1H, br s); 1.218 (9H, s).

Alcohol 1j (2.88 g; 20 mmol) was dissolved in TBME (20 mL) and treated with vinyl acetate (5.6 mL; 60 mmol; 3 equiv.) and Lipase PS-30 from *Pseudomonas cepacia* (100 mg; Amano International Enzyme Co.). The mixture was stirred at room temperature for 1 h and the enzyme was removed by filtration and the filtrate was concentrated to afford 3.21 g of a mixture of R-1j (90% ee) and S-2j (96% ee). The optical purities were determined by GC analysis using a chiral Cyclodex-B ™ column (J & W Scientific). The absolute configuration of 1j was determined by independent synthesis from S-epoxybutene and tert-butanol with acid catalysis using the procedure detailed above.

The mixture of R-1j and S-2j (approximately 10 mmol each) was dissolved in DCM (10 mL) and treated with triethylamine (2.09 mL; 15 mmol; 1.5 equiv.) and DMAP (12 mg; 0.1 mmol; 0.01 equiv.). The resulting solution was cooled to 0° and treated with succinic anhydride (1.05 g; 10.5 mmol; 1.05 equiv.) and stirred at room temperature overnight to completely consume 1j (tlc analysis). The reaction mixture was diluted with 1:1 ethyl acetate:hexanes (30 mL) and extracted with saturated aqueous NaHCO$_3$ (3×7 mL). The organic solution was concentrated and the residue was diluted with hexanes (30 mL) and extracted further with saturated aqueous NaHCO$_3$ (2×7 mL). The organic solution was dried (Na$_2$SO$_4$) and concentrated to afford S-2j (1.58 g; 85%) $^1$H nmr (CDCl$_3$): 5.824 (1H, ddd, J=5.70, 10.47, 16.40 Hz); 5.310 (1H, dt, J=1.14, 17.25 Hz); 5.163 (1H, dt, J=1.19, 10.46 Hz); 4.204 (1H, br q, J=3.23 Hz); 4.00 (1H, dd, J=4.96, 11.17 Hz); 3.938 (1H, dd, J=7.35, 11.15 Hz); 2.060 (3H, s); 1.197 (9H, s).

The combined aqueous extracts were acidified to pH 1 with HCl and extracted with DCM (2×15 mL) and ethyl acetate (2×15 mL). The combined extracts were dried (Na$_2$SO$_4$) and concentrated to afford succinate half-ester R-3j, 2.11 g (86%). $^1$H nmr (300 MHz, CDCl$_3$): 5.802 (1H, ddd, J=4.78, 11.29, 17.38 Hz); 5.295 (1H, dt, J=1.22, 17.39 Hz); 5.152 (1H, br d, J=10.66 Hz); 4.194 (1H, br q, J=5.59 Hz); 4.0 (2H, m); 2.65 (4H, m); 1.185 (9H, s).

Example 11

1-Hydroxy-2-phenoxy-3-butene (1k)

Phenol (1.88 g; 20 mmol) was dissolved in THF (40 mL) and tetrakis-(triphenylphosphine)palladium(0) (231 mg; 0.2 mmol; 0.01 equiv.) was added. The reaction mixture was cooled to 0° and epoxybutene (1.6 mL; 20 mmol; 1.0 equiv.) was added dropwise. The reaction mixture was stirred at 0° for 2 h, warmed to room temperature, and allowed to stir for 2 days. The reaction mixture was concentrated to afford a mixture of 1k and 4-phenoxy-2-butene-1-ol in a ratio of 69:31, respectively ($^1$H nmr analysis). The crude product was fractionated in vacuo to afford 1.59 g (48%) of 1k, bp 90°-95°/approximately 2 mm Hg. $^1$H nmr (300 MHz, CDCl$_3$): 7.298–7.246 (2H, m); 7.068–6.926 (3H, m); 5.844 (1H, ddd, J=5.88, 10.75, 17.13 Hz); 5.386 (1H, d, J=17.62 Hz); 5.321 (1H, d, J=10.90 Hz); 4.771 (1H, q, J=5.68 Hz); 3.791 (2H, d, J=4.94 Hz); 1.987 (1H, s). IR (neat film, cm$^{-1}$): 3400 (m); 2800 (m); 1600 (s); 1500 (s).

Alcohol 1k (0.82 g; 5.0 mmol) was dissolved in TBME (10 mL) and treated with vinyl acetate (1.38 mL; 15 mmol; 3 equiv.) and Lipase SAM-II (25 mg; Amano International Enzyme Co.). The mixture was stirred for 1.5 h and the enzyme was removed by filtration and the filtrate was concentrated to afford 0.867 g of a mixture of R-1k and S-2k.

The mixture of R-1k and S-2k (approximately 2.2 mmol each) was dissolved in DCM (10 mL) and treated with triethylamine (0.46 mL; 3.3 mmol; 1.5 equiv.) and DMAP (3 mg; 0.02 mmol; 0.01 equiv.). The resulting solution was treated with succinic anhydride (242 mg; 2.42 mmol; 1.1 equiv.) and stirred at room temperature to completely consume 1k (tlc analysis). The reaction mixture was diluted with ether (25 mL) and extracted with saturated aqueous NaHCO$_3$ (2×15 mL). The organic solution was dried (MgSO$_4$) and concentrated to afford S-2k (366 mg; 81%). $^1$H nmr (300 MHz, CDCl$_3$): 7.293–7.241 (2H, m); 6.980–6.916 (3H, m); 5.868 (1H, ddd, J=5.79, 10.72, 16.65 Hz); 5.433 (1H, d, J=17.56 Hz); 5.330 (1H, d, J=10.47 Hz); 4.880 (1H, q, J=5.22 Hz); 4.275 (2H, d, J=6.30 Hz); 2.069 (3H, s).

The combined aqueous extracts were acidified to pH 1 with HCl and extracted with ether (3×15 mL). The combined extracts were dried (MgSO$_4$) and concentrated to afford succinate half-ester R-3k, 104 mg (18%). $^1$H nmr (300 MHz, CDCl$_3$): 7.296–7.244 (2H, m); 6.983–6.916 (3H, m); 5.864 (1H, ddd, J=5.73, 10.58, 16.88 Hz); 5.424 (1H, d, J=17.40 Hz); 5.335 (1H, d, J=10.61 Hz); 4.886 (1H, q, J=5.66 Hz); 4.340 (1H, dd, J=6.71, 11.60 Hz); 4.292 (1H, dd, J=4.45, 11.72 Hz); 2.704–2.607 (4H, m). IR (neat film, cm$^{-1}$): 3000 (s); 2500 (s); 1750 (s).

This half-ester R-3k (104 mg; 0.4 mmol) was dissolved in methanol (5 mL) and treated with potassium carbonate (110 mg; 0.8 mmol; 2 equiv.) and stirred overnight to completely consume 3k (tlc analysis). The reaction mixture was diluted with water (25 mL) and ether (25 mL) and the layers were separated. The aqueous layer was extracted with ether (2×15 mL). The combined organic solution was dried (MgSO$_4$) and concentrated to afford 62 mg (94%) of R-1k. All achiral properties of 1k are as reported above. $[\alpha]_D^{20}$ −14.2° (C. 1.01, CH$_3$OH). The absolute configuration of 1k was inferred to be R-(−) by analogy with the absolute configuration results of the enzymatic reaction of 1j. $^1$H nmr analysis of the MTPA ester using an analogous procedure to that of Dale et al., *J. Org. Chem.*, 1969, 34, 2543, indicated 54% ee for R-1k.

The acetate S-2k (366 mg; 1.8 mmol) was deacetylated by overnight treatment with potassium carbonate (497 mg; 3.6 mmol; 2 equiv.) in methanol (5 mL). The product S-1k (260 mg; 88%) was isolated by dilution with water (25 mL), extraction with ether (3×10 mL), drying of the extracts (MgSO$_4$), and concentration. All achiral properties of 1k are as reported above. $^1$H nmr analysis of the MTPA ester using an analogous procedure to that of Dale et al., *J. Org. Chem.*, 1969, 34, 2543, indicated 94% ee for S-1k. $[\alpha]_D^{20}$ +21.0° (c. 1.025, CH$_3$OH).

The next two examples use cyclic secondary alcohols.

Example 12 trans-2-Phenylcyclohexanol (1m)

Magnesium turnings (706 mg; 29 mmol; 1.45 equiv.) were combined with THF (3.5 mL). Bromobenzene (3.1 mL; 29.4 mmol; 1.47 equiv.) in 5 mL of THF was added slowly dropwise. After approximately 1 mL of the bromobenzene solution had been added 1 drop of 1,2-dibromoethane was added to initiate the reaction. Once all the bromobenzene was added and the magnesium consumed the reaction mixture was diluted with THF (20 mL) and cooled to −30° Copper(I) chloride (130 mg; 1.32 mmol; 0.066 equiv.) was added and the reaction mixture was stirred for 10 min. A solution of cyclohexene oxide (2.1 mL; 20 mmol) in THF (2 mL) was added slowly dropwise. After the addition was complete the reaction mixture was warmed to 0° and stirred for 2 h. The reaction mixture was then treated with saturated aqueous ammonium sulfate (10 mL) and the layers were separated. The organic layer was washed with 5 mL portions of saturated ammonium sulfate until the washes were colorless. The combined aqueous washes were extracted with ether (3×10 mL), and the combined organic solution was dried (MgSO$_4$) and concentrated. The crude product was recrystallized from pentane to afford 850 mg (24%) of 1m as white crystals. $^1$H nmr (300 MHz, CDCl$_3$): 7.369–7.221 (5H, m); 3.640 (1H, m); 2.438 (1H, dt, J=10.43 Hz, 3.34 Hz); 2.146–2.114 (1H, m); 1.892–1.847 (2H, m); 1.788–1.753 (1H, m); 1.639 (1H, s); 1.530–1.254 (4H, m). IR (KBr, cm$^{-1}$): 3500 (s); 2900 (s); 1600 (m). FDMS (m/e): 176 (M+).

Alcohol 1m (834 mg; 4.7 mmol) was dissolved in DCM (10 mL) and triethylamine (979 mL; 7.05 mmol; 1.5 equiv.) and DMAP (28 mg; 0.235 mmol; 0.05 equiv.) were added. The resulting solution was cooled to 0° and chloroacetic anhydride (959 mg; 5.64 mmol; 1.2 equiv.) was added. The reaction mixture was stirred at room temperature to consume 1m (tlc analysis) and diluted with water (25 mL) and ether (25 mL). The layers were separated and the organic solution was washed with 1N HCl (2×10 mL) and saturated NaHCO$_3$ (10 mL), dried (MgSO$_4$), and concentrated to afford crude 2m'. The crude product was flash chromatographed and eluted with 1:9 ether:hexanes to afford 984 mg (83%) of 2m'. $^1$H nmr (300 MHz, CDCl$_3$): 7.489–7.165 (5H, m); 5.042 (1H, m); 3.798 (1H, d, J=14.80 Hz); 3.686 (1H, d, J=14.80 Hz); 2.733–2.644 (1H, m); 2.168–2.155 (1H, m); 1.980–1.780 (4H, m); 1.653–1.375 (4H, m). IR (neat film, cm$^{-1}$): 3100 (w); 2900 (s); 1750 (s); 1550 (w). FDMS (m/e): 252 (M+).

Racemic chloroacetate 2m' (756 mg; 3.0 mmol) was combined with 25 g of pH 7 phosphate buffer and the pH was equilibrated to 7.00. Lipase PS-30 from *Pseudomonas cepacia* (60 mg; Amano International Enzyme Co.) was added and the hydrolysis commenced. The reaction was performed under constant pH conditions using an automatic titrator and the reaction was followed by uptake of 1.000N NaOH. After 2 days the reaction was halted by extraction with ether. The extracts were dried (MgSO$_4$) and concentrated to afford 617 mg of the mixture of 1R,2S-1m and 1S,2R-2m'.

The mixture of 1R,2S-1m and 1S,2R-2m' (approximately 1.5 mmol each) was dissolved in DCM (15 mL) and treated with triethylamine (627 mL; 4.5 mmol; 3 equiv.) and DMAP (4 mg; 0.03 mmol; 0.02 equiv.). The mixture was treated with succinic anhydride (330 mg;

3.3 mmol; 2.2 equiv.) and stirred at room temperature to completely consume 1m (tlc analysis). The reaction mixture was diluted with ether and washed with 1$\underline{N}$ HCl (10 mL) and the wash was discarded. The ether layer was extracted with saturated aqueous NaHCO$_3$ (3×10 mL). The organic solution was dried (MgSO$_4$) and concentrated to afford 1S,2R-2m' (53 mg; 14%). All achiral properties of 2m' are as reported above.

The combined aqueous extracts were acidified to pH 1 with HCl and extracted with ether (3×10 mL). The combined extracts were dried (MgSO$_4$) and concentrated to afford succinate half-ester 1R,2S-3m, 162 mg (39%). $^1$H nmr (300 MHz, CDCl$_3$): 7.272–7.161 (5H,m); 5.063–4.915 (1H, m); 2.693–2.654 (1H, m); 2.410–2.388 (1H, m); 1.914–1.754 (4H, m); 1.586–1.243 (4H, m).

The half-ester 1R,2S-3m (162 mg; 0.59 mmol) was dissolved in methanol (5 mL) and treated with potassium carbonate (163 mg; 1.18 mmol; 2 equiv.) and stirred overnight to completely consume 3m (tlc analysis). The reaction mixture was diluted with water (15 mL) and extracted three times with ether. The combined extracts were dried (MgSO$_4$) and concentrated to afford 89 mg (86%) of 1R,2S-1m. All achiral properties of 1m are as reported above. $[\alpha]_D^{20}$ −40.6° (c. 1.10, CH$_3$OH). The absolute configuration of 1m is known to be 1S,2R-(+) (Laumen, Ph.D. Thesis, Bergische Universitat at Wuppertal, 1987, p. 234). GC analysis using a chiral CYCLODEX-B ™ column (J & W Scientific) indicated 58% ee for 1R,2S-1m.

The chloroacetate 1S,2R-2m' (53 mg; 0.21 mmol) was deacylated by overnight treatment with potassium carbonate (58 mg; 0.42 mmol; 2 equiv.) in methanol (5 mL). The product 1S,2R-1m (29 mg; 78%) was isolated by dilution with water (15 mL), extraction three times with ether, drying of the extracts (MgSO$_4$), and concentration. All achiral properties of 1m are as reported above. $[\alpha]_D^{20}$ +43.8° (c. 1.335, CH$_3$OH). GC analysis using a chiral CYCLODEX-B ™ column (J & W Scientific) indicated 84% ee for 1S,2R-1m.

Example 13 trans-Cyclopentane-1,2-diol monoacetate (1n)

Cyclopentene oxide (4.36 mL; 50 mmol) was added to a 10% solution of sodium hydroxide in water (25 mL) and the resulting solution was heated to reflux for 45 min to completely consume the epoxide (tlc analysis). The crude product was isolated by continuous extraction with TBME followed by removal of the solvent. The crude product was distilled in vacuo to afford 2.06 g (40%) of trans-cyclopentane-1,2-diol (4), bp 140° C./approximately 2 mm Hg. $^1$H nmr (300 MHz, CDCl$_3$): 4.0 (2H, t, J=4.58 Hz); 3.0 (2H, br s); 1.984 (2H, m[apparent 6], J=6.43 Hz); 1.712 (2H, m(5), J=7.34 Hz); 1.534 (2H, m(5), J=7.08 Hz). EIMS (m/e): 102, 84, 73, 57, 55, 43, 41.

Diol 4 (1.53 g; 15 mmol) was dissolved in DCM (10 mL) and triethylamine (3.2 mL; 22.5 mmol; 1.5 equiv.) and DMAP (92 mg; 0.75 mmol; 0.05 equiv.) were added. The resulting solution was cooled to 0°, acetic anhydride (3.4 mL; 36 mmol; 2.4 equiv.) was added, and the reaction mixture was allowed to warm to room temperature overnight. The reaction mixture was diluted with water (25 mL) and ether (25 mL) and the layers were separated. The organic layer was washed with 1$\underline{N}$ HCl (15 mL) and saturated aqueous NaHCO$_3$ (2×15 mL), dried (MgSO$_4$), and concentrated to afford 1.92 g (69%) of diacetate 2n. $^1$H nmr (300 MHz, CDCl$_3$): 5.058 (2H, br t, J=4.30 Hz); 2.10 (2H, m); 2.034 (6H, s); 1.762 (2H, m(5), J=7.25 Hz); 1.6 (2H, m). EIMS (m/e): 186, 143, 126, 101, 84, 83, 43.

Racemic diacetate 2n (1.86 g; 10 mmol) was combined with pH 7 phosphate buffer (25 mL) and the pH was equilibrated to 7.00. Lipase SAM-II (200 mg) (Amano International Enzyme Co.) was added and the resulting hydrolysis was performed under constant pH conditions (automatic titrator) and followed by the uptake of 1.000$\underline{N}$ NaOH. At approximately 50% conversion the reaction was halted by extraction three times with ether. The combined extracts were dried (MgSO$_4$) and concentrated to afford R,R-1n and S,S-2n (1.31 g). The reaction as performed is known to give the above absolute configurations (Laumen, Ph.D. Thesis, Bergische Universitat at Wuppertal, 1987, p. 220–222).

The mixture of R,R-1n and S,S-2n (approximately 5 mmol each) was dissolved in DCM (5 mL) and treated with triethylamine (1.05 mL; 7.5 mmol; 1.5 equiv.) and DMAP (6 mg; 0.05 mmol; 0.01 equiv.). The mixture was treated with succinic anhydride (551 mg; 5.5 mmol; 1.1 equiv.) and stirred at room temperature to completely consume 1n (tlc analysis). The reaction mixture was diluted with ether (25 mL) and extracted with saturated aqueous NaHCO$_3$ (2×15 mL). The organic solution was dried (MgSO$_4$) and concentrated to afford S,S-2n (852 mg; 92%). All achiral properties of 2n are as reported above.

The combined aqueous extracts were acidified to pH 1 with HCl and extracted with ether (3×15 mL). The combined extracts were dried (MgSO$_4$) and concentrated to afford succinate half-ester R,R-3n, 504 mg (41%). $^1$H nmr (300 MHz, CDCl$_3$): 5.1 (2H, m); 2.65 (4H, m); 2.095 (2H, m(5), J=6.74 Hz); 2.035 (3H, s); 1.766 (2H, m(5), J=7.26 Hz); 1.65 (2H, m). FDMS (m/e): 245 (MH+).

The half-ester R,R 3n (488 mg; 2.0 mmol) was dissolved in methanol (5 mL) and treated with potassium carbonate (1.10 g; 8.0 mmol; 4 equiv.) and stirred overnight to completely consume 3n (tlc analysis). The solvent was removed at reduced pressure and the residue was triturated with ethyl acetate and DCM. The mixture was filtered and the filtrate was concentrated to afford R,R-4, 192 mg (94%). All achiral properties of 4 are as reported above. $[\alpha]_D^{20}$ −16.5° (c. 1.01, CH$_3$OH). Conversion to the monoacetate R,R-1n and GC analysis on a chiral CYCLODEX-B ™ column indicated 90% ee for R,R-1n (and R,R-4).

The diacetate S,S-2n (558 mg; 3.0 mmol) was exhaustively deacetylated by overnight treatment with potassium carbonate (1.66 g; 12.0 mmol; 4 equiv.) in methanol (5 mL). The product S,S-4 (300 mg; 98%) was isolated by concentration of the reaction mixture, trituration of the residue with ethyl acetate and DCM, filtration, drying (MgSO$_4$), and concentration of the filtrate. All achiral properties of 4 are as reported above. $[\alpha]_D^{20}$ +17.4° (c. 1.17, CH$_3$OH). Conversion to the monoacetate S,S-1n and GC analysis on a chiral CYCLODEX-B ™ column indicated 88% ee for S,S-1n (and S,S-4).

The following example demonstrates conversion of the succinate monoester to the parent alcohol without isolation.

Example 14

1-Phenylethanol (1a)

The mixture of S-1a and R-2a (approximately 3 mmol each) generated as described above (Example 1) was dissolved in DCM (5 mL) and treated with triethylamine (627 mL; 4.5 mmol; 1.5 equiv.) and DMAP (6 mg; 0.03 mmol; 0.01 equiv.). The resulting solution was treated with succinic anhydride (330 mg; 3.3 mmol; 1.1 equiv.) and stirred at room temperature to completely consume 1a (tlc analysis). The reaction mixture was diluted with ether (25 mL), washed with 1N HCl (10 mL) and the wash was discarded. The ethereal solution was extracted with saturated aqueous NaHCO₃ (3×10 mL), dried (MgSO₄), and concentrated to afford R-2a (419 mg; 85%) All properties of 2a are as reported in Example 1.

The combined aqueous extracts were shaken with 10% NaOH (15 mL), and then extracted with ether (2×25 mL) and DCM (25 mL). The combined organic extracts were dried (MgSO₄) and concentrated to afford alcohol S-1a, 293 mg (80%). All properties of 1a are as reported in Example 1. $^1$H nmr analysis of the MTPA ester using an analogous procedure to that of Dale et al., *J. Org. Chem.*, 1969, 34, 2543, indicated 96% ee for S-1a.

The acetate R-2a (230 mg; 1.4 mmol) was deacetylated by overnight treatment with potassium carbonate (386 mg; 2.8 mmol; 2 equiv.) in methanol (15 mL). The product R-1a (137 mg; 80%) was isolated by dilution with water (15 mL), extraction three times with ether, drying of the extracts (MgSO₄), and concentration. All properties of 1a are as reported in Example 1. $^1$H nmr analysis of the MTPA ester using an analogous procedure to that of Dale et al., *J. Org. Chem.*, 1969, 34, 2543, indicated 96% ee for R-1a.

The following two examples illustrate the use of different cyclic anhydrides.

Example 15

1-Phenylethanol (1a) with Maleic Anhydride

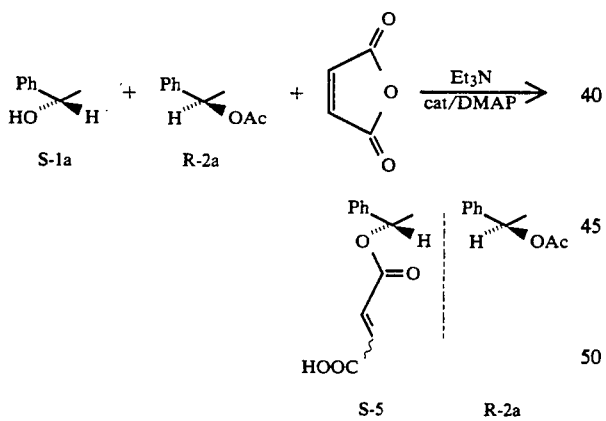

The mixture of S-1a and R-2a (approximately 2 mmol each) prepared as per Example 1 was dissolved in DCM (5 mL) and treated with triethylamine (418 mL; 3 mmol; 1.5 equiv.) and DMAP (3 mg; 0.02 mmol; 0.01 equiv.). The resulting solution was cooled to 0° and was treated with maleic anhydride (216 mg; 2.2 mmol; 1.1 equiv.) and allowed to warm to room temperature to completely consume 1a (tlc analysis). The reaction mixture was diluted with ether (25 mL) and extracted with saturated aqueous NaHCO₃ (3×10 mL). The organic solution was dried (MgSO₄) and concentrated to afford R-2a (298 mg; 91%) All physical properties of 2a are as reported in Example 1.

The combined aqueous extracts were acidified to pH 1 with HCl and extracted with DCM (2×10 mL) and ethyl acetate (2×10 mL). The combined extracts were dried (MgSO₄) and concentrated to afford maleate half-ester S-5 as a mixture of cis and trans isomers, 400 mg (91%). cis-S-5: $^1$H nmr (300 MHz, CDCl₃): 7.378–7.261 (5H, m); 6.462 (1H, d, J=12.75 Hz); 6.386 (1H, d, J=12.81 Hz); 6.022 (1H, q, J=6.6 Hz); 1.657 (3H, d, J=6.6 Hz). trans-S-5: $^1$H nmr (300 MHz, CDCl₃): 7.378–7.261 (5H, m); 6.943 (1H, d, J=15.72 Hz); 6.846 (1H, d, J=15.71 Hz); 5.977 (1H, q J=6.6 Hz); 1.609 (3H, d, J=6.6 Hz). FDMS (m/e): 221 (MH+).

This half-ester S-5 (110 mg; 0.5 mmol) was dissolved in methanol (2 mL) and treated with potassium carbonate (138 mg; 1.0 mmol; 2 equiv.). The reaction mixture was stirred overnight and then diluted with water (25 mL) and extracted with ether (3×10 mL). The combined extracts were dried (MgSO₄) and concentrated to afford 59 mg (97%) of S-1a. All properties of 1a are as reported in Example 1. $^1$H nmr analysis of the MTPA ester using an analogous procedure to that of Dale et al., *J. Org. Chem.*, 1969, 34, 2543, indicated 92% ee for S-1a.

Acetate R-2a (82 mg; 0.5 mmol) was deacetylated by overnight treatment with potassium carbonate (138 mg; 1.0 mmol; 2 equiv.) in methanol (2 mL). The product R-1a (56 mg; 92%) was isolated by dilution with water (25 mL), extraction with ether (3×10 mL), drying of the extracts (MgSO₄), and concentration. All properties of 1a are as reported in Example 1. $^1$H nmr analysis of the MTPA ester using an analogous procedure to that of Dale et al., *J. Org. Chem.*, 1969, 34, 2543, indicated 86% ee for R-1a.

Example 16

1-Phenylethanol (1a) with Phthalic Anhydride

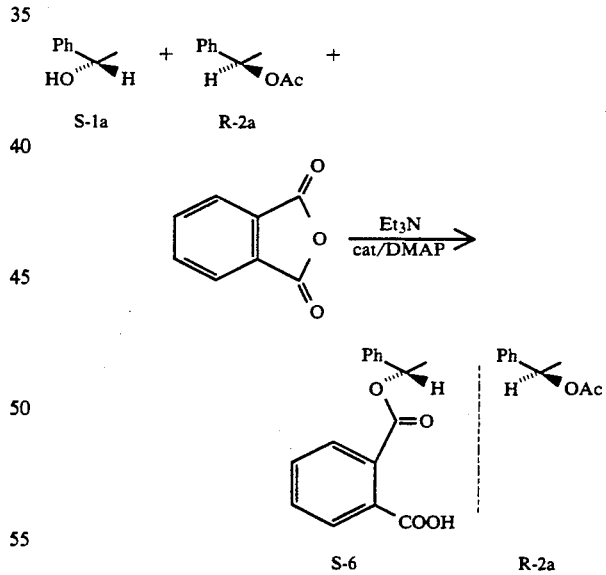

The mixture of S-1a and R-2a (approximately 2 mmol each) prepared as per Example 1 was dissolved in DCM (5 mL) and treated with triethylamine (418 mL; 3 mmol; 1.5 equiv.) and DMAP (3 mg; 0.02 mmol; 0.01 equiv.). The resulting solution was cooled to 0° and was treated with phthalic anhydride (326 mg; 2.2 mmol; 1.1 equiv.) and allowed to warm to room temperature to completely consume 1a (tlc analysis). The reaction mixture was diluted with ether and extracted with saturated aqueous NaHCO₃ (3×10 mL). The organic solution was dried (MgSO₄) and concentrated to afford R-2a (311 mg; 95%) All physical properties of 2a are as reported in Example 1.

The combined aqueous extracts were acidified to pH 1 with HCl and extracted with DCM (2×10 mL) and ether (2×10 mL). The combined extracts were dried (MgSO$_4$) and concentrated to afford phthalate half-ester S-6, 535 mg (99%). $^1$H nmr (300 MHz, CDCl$_3$): 7.906-7.247 (9H, m); 6.147 (1H, q, J=6.6 Hz); 1.666 (3H, d, J=6.6 Hz). IR (neat film, cm$^{-1}$): 3000 (s); 2600 (m); 1740 (s); 1590 (m). FDMS (m/e): 270 (M+).

This half-ester S-6 (270 mg; 1.0 mmol) was dissolved in methanol (3 mL) and treated with potassium carbonate (276 mg; 2.0 mmol; 2 equiv.) and stirred overnight to completely consume 6 (tlc analysis). The reaction mixture was diluted with water (25 mL) and extracted with ether (3×10 mL). The combined extracts were dried (MgSO$_4$) and concentrated to afford 60 mg (49%) of S-1a. All properties of 1a are as reported in Example 1. $^1$H nmr analysis of the MTPA ester using an analogous procedure to that of Dale et al., *J. Org. Chem.*, 1969, 34, 2543, indicated 98% ee for S-1a.

The acetate R-2a (164 mg; 1.0 mmol) was deacetylated by overnight treatment with potassium carbonate (276 mg; 2.0 mmol; 2 equiv.) in methanol (3 mL). The product R-1a (107 mg; 88%) was isolated by dilution with water (25 mL), extraction with ether (3×10 mL), drying of the extracts (MgSO$_4$), and concentration. All properties of 1a are as reported in Example 1. $^1$H nmr analysis of the MTPA ester using an analogous procedure to that of Dale et al., *J. Org. Chem.*, 1969, 34, 2543, indicated 90% ee for R-1a.

Example 17

Ethylene Glycol Monobenzyl Ether (7)

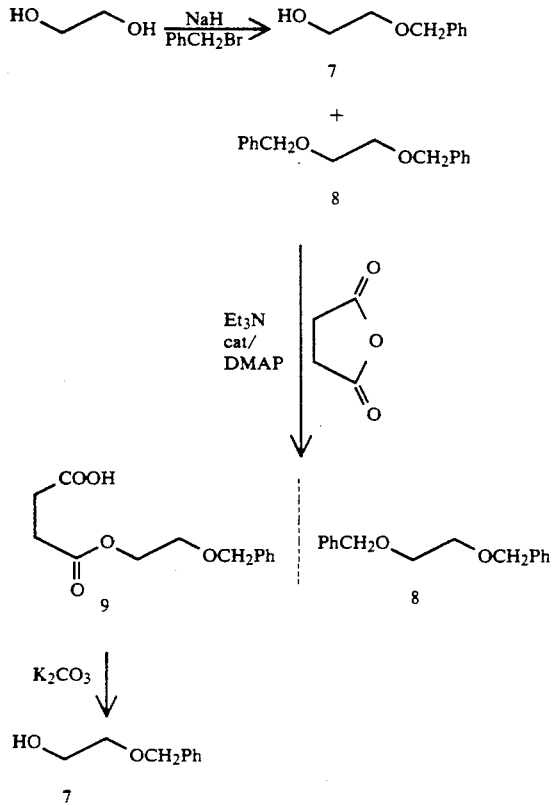

An 80 wt. percent suspension of sodium hydride in mineral oil (360 mg; 12 mmol; 1.2 equiv.) was slurried in THF (20 mL) and cooled to 0°. Ethylene glycol (556 mL; 10 mmol) was added and the reaction mixture was stirred for 15 min. Benzyl bromide (1.19 mL; 10 mmol; 1.0 equiv.) and tetrabutylammonium iodide (184 mg; 0.5 mmol; 0.05 equiv.) were added and the reaction mixture was stirred overnight at room temperature. The reaction mixture was poured into ice water (25 mL) and extracted with ether (3×15 mL). The combined extracts were dried (MgSO$_4$) and concentrated to afford 1.45 g of a mixture of ethylene glycol monobenzyl ether (7) and ethylene glycol dibenzyl ether (8).

The mixture of 7 and 8 (approximately 3 mmol 7) was dissolved in DCM (15 mL) and treated with triethylamine (627 mL; 4.5 mmol; 1.5 equiv.) and DMAP (4 mg; 0.03 mmol; 0.01 equiv.). Succinic anhydride (330 mg; 1.1 equiv.) was added and the reaction mixture was stirred at room temperature to completely consume 7. The reaction mixture was diluted with ether (25 mL) and washed with 1N HCl (10 mL) and the wash was discarded. The organic solution was extracted with saturated aqueous NaHCO$_3$ (3×10 mL), dried (MgSO$_4$) and concentrated to afford 8. $^1$H nmr (300 MHz, CDCl$_3$): 7.357-7.279 (10H, m); 4.587 (4H, s); 3.668 (4H, s).

The aqueous bicarbonate extracts were acidified to pH 1 with 1N HCl and extracted with ether (3×10 mL). The combined extracts were dried (MgSO$_4$) and concentrated to afford succinate monoester 9 (212 mg; approximately 28%). $^1$H nmr (300 MHz, CDCl$_3$): 7.351-7.291 (5H, m); 4.565 (2H, s); 4.286 (2H, t, J=4.54 Hz); 3.674 (2H, t, J=4.78 Hz); 2.678 (4H, s). IR (neat film, cm$^{-1}$): 3000 (s); 1750 (s). FDMS (m/e): 252 (M+).

Succinate monoester 9 (71 mg; 0.28 mmol) was dissolved in methanol (5 mL) and treated with potassium carbonate (77 mg; 0.56 mmol; 2 equiv.). After complete consumption of 9 (tlc analysis), the reaction mixture was diluted with water and extracted three times with ether. The combined extracts were dried (MgSO$_4$) and concentrated to afford 7. $^1$H nmr (300 MHz, CDCl$_3$): 7.393-7.245 (5H, m); 4.572 (2H, s); 3.779-3.765 (2H, m); 3.625-3.595 (2H, m). IR (neat film, cm$^{-1}$): 3400 (s); 2900 (s); 1500 (w). EIMS (m/e): 152 (M+).

The invention has been described above with particular reference to preferred embodiments. A skilled practitioner familiar with the above-detailed description can make many modifications without departing from the scope and spirit of the invention.

What is claimed is:

1. A method for the purification of an alcohol comprising the sequential steps of:

(a) contacting an organic solution comprising an organic-soluble impurity and a crude parent alcohol with a cyclic anhydride to form a mixture comprising a corresponding alcohol half-ester and said organic-soluble impurity wherein said half-ester substituent is derived from the cyclic anhydride;

(b) combining said mixture with a base in an aqueous environment wherein said half-ester forms a water-soluble salt;

(c) separating said water-soluble salt from said organic-soluble impurity; and (d) removing said half-ester substituent from said water-soluble salt to afford a purified parent alcohol.

2. A method according to claim 1 where said crude parent alcohol of the crude alcohol solution is defined by the formula $R^1OH$ wherein $R^1$ represents a substituted or unsubstituted $C_1$–$C_{20}$ alkyl, $C_3$–$C_{20}$ cycloalkyl, heterocyclic, or cycloalkenyl, $C_8$–$C_{20}$ cycloalkynyl, $C_2$–$C_{20}$ alkenyl, $C_2$–$C_{20}$ alkynyl group, or $C_4$–$C_{20}$ aromatic or heteroaromatic group wherein said hetero atom is be selected from the group consisting of 0, S, or N and said substituent is selected from the group consisting of a halogen, a cyano, a $C_1$–$C_{20}$ alkyl, a $C_2$–$C_{20}$ alkenyl, a $C_4$–$C_{20}$ aromatic, a $C_1$–$C_{20}$ ether, a $C_1$–$C_{20}$ ester, a $C_1$–$C_{20}$ sulfonate ester, a nitro, a $C_1$–$C_{20}$ ketone, or a $C_1$–$C_{20}$ thioether.

3. A method according to claim 2 wherein said crude parent alcohol is chiral and said impurity comprises an antipodal ester corresponding to said alcohol.

4. A method according to claim 3 wherein said crude parent alcohol is represented by $R^1OH$ where $R^1$ is 1-phenylethyl, 1-phenyl-2-propyl, 1-phenyl-3-butyl, 1-phenylthio-3-butyl, 1-phenoxy-2-propyl, 1-adamantylethyl, 1-tosyloxy-3-buten-2-yl, 2-tert-butoxy-3-buten-1-yl, 2-phenoxyl-3-buten-1-yl, trans-2-phenylcyclohyexyl, and trans-2-acetoxycyclopentyl.

5. A method according to claim 4 wherein said anhydride is a $C_2$–$C_{20}$ cyclic anhydride.

6. A method according to claim 5 wherein said anhydride is selected from the group consisting of succinic anhydride, phthalic anhydride, or maleic anhydride.

7. A method according to claim 6 wherein said anhydride is succinic anhydride.

8. A method according to claim 7 wherein the conjugate acid of said base has a pKa within a range of 7 to 25.

9. A method according to claim 8 wherein the conjugate acid of said base has a pKa within the range of 7 to 14 and is selected from the group consisting of KOH, NaOH, $K_2CO_3$, $KHCO_3$, $Na_2CO_3$, and $NaHCO_3$.

10. A method according to claim 9 wherein the base is either $KHCO_3$ or $NaHCO_3$.

11. A method according to claim 10 wherein said alcohol half ester is separated from the aqueous solution by acidification of said solution to a pH < about 3 and extraction with an organic solvent.

12. A method according to claim 11 wherein in step (d) said alcohol is regenerated by treatment of said half-ester with a base or an acid.

13. A method according to claim 12 wherein said alcohol half ester is separated from the aqueous solution by acidification of said solution to a pH < about 3 and extraction with an organic solvent.

14. A method according to claim 1 wherein the base is either $KHCO_3$ or $NaHCO_3$.

15. A method according to claim 14 wherein in step (d) said alcohol is regenerated by treatment of said half ester with a base or an acid.

16. A method according to claim 1 wherein in step (d) said alcohol is regenerated by treatment of said half-ester with a base or an acid.

17. A method according to claim 16 wherein said alcohol is chiral and said impurity comprises a antipodal ester corresponding to said alcohol, wherein said alcohol and antipodal ester result from an enzymatic kinetic resolution.

* * * * *